(12) United States Patent
Gualberto et al.

(10) Patent No.: US 7,618,626 B2
(45) Date of Patent: Nov. 17, 2009

(54) COMBINATION TREATMENT FOR NON-HEMATOLOGIC MALIGNANCIES

(75) Inventors: Antonio Gualberto, East Greenwich, RI (US); Bruce D. Cohen, East Lyme, CT (US); Carrie L. Melvin, Wayland, MA (US); M. Luisa Roberts, Noank, CT (US)

(73) Assignee: Pfizer Inc, New York, NY (US)

( * ) Notice: Subject to any disclaimer, the term of this patent is extended or adjusted under 35 U.S.C. 154(b) by 7 days.

(21) Appl. No.: 11/182,343

(22) Filed: Jul. 15, 2005

(65) Prior Publication Data

US 2006/0018910 A1 Jan. 26, 2006

Related U.S. Application Data

(60) Provisional application No. 60/588,721, filed on Jul. 16, 2004.

(51) Int. Cl.
*A61K 39/395* (2006.01)

(52) U.S. Cl. .................. 424/130.1; 424/143.1

(58) Field of Classification Search .................. None
See application file for complete search history.

(56) References Cited

U.S. PATENT DOCUMENTS

| | | | |
|---|---|---|---|
| 4,399,216 A | 8/1983 | Axel et al. ................ 435/6 |
| 4,510,245 A | 4/1985 | Cousens et al. .......... 435/172.3 |
| 4,634,665 A | 1/1987 | Axel et al. ............... 435/68 |
| 4,740,461 A | 4/1988 | Kaufman ................. 435/68 |
| 4,912,040 A | 3/1990 | Kaufman et al. ......... 435/69.6 |
| 4,959,455 A | 9/1990 | Clark et al. .............. 530/351 |
| 4,968,516 A | 11/1990 | Koszinoski et al. ...... 435/172.3 |
| 5,151,510 A | 9/1992 | Stec et al. ............... 536/27 |
| 5,168,062 A | 12/1992 | Stinski ................... 435/240.2 |
| 5,179,017 A | 1/1993 | Axel et al. ............... 435/240.2 |
| 5,223,409 A | 6/1993 | Ladner et al. ............ 435/69.7 |
| 5,530,101 A | 6/1996 | Queen et al. ............ 530/387.3 |
| 5,545,806 A | 8/1996 | Lonberg et al. .......... 800/2 |
| 5,545,807 A | 8/1996 | Surani et al. ............ 800/2 |
| 5,585,089 A | 12/1996 | Queen et al. ............ 424/133.1 |
| 5,587,458 A | 12/1996 | King et al. .............. 530/387.3 |
| 5,591,669 A | 1/1997 | Krimpenfort et al. ..... 800/2 |
| 5,612,205 A | 3/1997 | Kay et al. ............... 435/172.3 |
| 5,625,126 A | 4/1997 | Lonberg et al. .......... 800/2 |
| 5,625,825 A | 4/1997 | Rostoker et al. ......... 395/730 |
| 5,633,425 A | 5/1997 | Lonberg et al. .......... 800/2 |
| 5,643,763 A | 7/1997 | Dunn et al. .............. 435/91.1 |
| 5,661,016 A | 8/1997 | Lonberg et al. .......... 435/172.3 |
| 5,693,761 A | 12/1997 | Queen et al. ............ 536/23.53 |
| 5,693,792 A | 12/1997 | Torii et al. .............. 540/358 |
| 5,714,350 A | 2/1998 | Co et al. ................. 435/69.6 |
| 5,721,367 A | 2/1998 | Kay et al. ............... 800/2 |
| 5,741,957 A | 4/1998 | Deboer et al. ........... 800/2 |
| 5,747,498 A | 5/1998 | Schnuer ................. 514/259 |
| 5,750,172 A | 5/1998 | Meade et al. ............ 426/580 |
| 5,756,687 A | 5/1998 | Denman et al. .......... 530/412 |
| 5,770,429 A | 6/1998 | Lonberg et al. .......... 435/240.2 |
| 5,777,085 A | 7/1998 | Co et al. ................. 530/388.23 |
| 5,789,215 A | 8/1998 | Berns et al. ............. 435/172.3 |
| 5,789,650 A | 8/1998 | Lonberg et al. .......... 800/2 |
| 5,792,783 A | 8/1998 | Tang et al. .............. 514/397 |
| 5,814,318 A | 9/1998 | Lonberg et al. .......... 424/184.1 |
| 5,827,690 A | 10/1998 | Meade et al. ............ 435/69.6 |
| 5,834,504 A | 11/1998 | Tang et al. .............. 514/418 |
| 5,861,510 A | 1/1999 | Piscopio et al. .......... 544/131 |
| 5,863,949 A | 1/1999 | Robinson et al. ......... 514/575 |
| 5,877,305 A | 3/1999 | Huston et al. ........... 536/23.53 |
| 5,883,113 A | 3/1999 | Tang et al. .............. 514/418 |
| 5,886,020 A | 3/1999 | Tang et al. .............. 514/418 |
| 5,886,152 A | 3/1999 | Nakatani et al. ......... 530/387.3 |
| 5,916,771 A | 6/1999 | Hori et al. .............. 435/69.6 |
| 5,939,598 A | 8/1999 | Kucherlapati et al. ..... 800/25 |
| 5,985,615 A | 11/1999 | Jakobovits et al. ....... 435/69.6 |
| 5,994,619 A | 11/1999 | Stice et al. .............. 800/21 |
| 5,998,209 A | 12/1999 | Jokobovits et al. ....... 435/463 |
| 6,054,297 A | 4/2000 | Carter et al. ............. 435/69.6 |
| 6,054,561 A | 4/2000 | Ring |
| 6,075,181 A | 6/2000 | Kucherlapati et al. ..... 800/25 |
| 6,084,085 A | 7/2000 | Baserga et al. .......... 536/23.5 |
| 6,091,001 A | 7/2000 | Jakobovits et al. ....... 800/18 |
| 6,114,598 A | 9/2000 | Kucherlapati et al. ..... 800/18 |
| 6,130,364 A | 10/2000 | Jakobovits et al. ....... 800/6 |
| 6,146,629 A | 11/2000 | Dagan et al. ............ 424/149.1 |
| 6,657,103 B1 | 12/2003 | Kucherlapati et al. |
| 2003/0165502 A1 | 9/2003 | Fujita-Yamaguchi |
| 2003/0235582 A1 | 12/2003 | Singh ................... 424/141.1 |
| 2004/0086503 A1 | 5/2004 | Cohen et al. ............ 424/143.1 |
| 2004/0202655 A1 | 10/2004 | Morton et al. .......... 424/143.1 |
| 2004/0228859 A1* | 11/2004 | Graus et al. ............ 424/143.1 |
| 2005/0069539 A1 | 3/2005 | Cohen et al. ............ 424/141.1 |

FOREIGN PATENT DOCUMENTS

EP 0216846 4/1987

(Continued)

OTHER PUBLICATIONS

DiGiovanni, John, et al., "Deregulated expression of insulin-like growth factor I in prostate epithelium leads to neoplasia in transgenic mice," Proc. Natl. Acad. Sci. USA, 97:3455-3460 (2000).

(Continued)

*Primary Examiner*—Misook Yu
*Assistant Examiner*—Mark Halvorson
(74) *Attorney, Agent, or Firm*—Austin W. Zhang; Bryan C. Zielinski

(57) ABSTRACT

The present invention relates to a therapeutic method for the treatment of non-hematologic malignancies comprising administering anti-IGF-1R antibodies, particularly human anti-IGF-1R antibodies, to a patient, in conjunction with the administration of at least one other therapeutic agent. The invention further relates to pharmaceutical compositions comprising these antibodies and methods of using such compositions thereof for treatment.

5 Claims, 11 Drawing Sheets

FOREIGN PATENT DOCUMENTS

| | | |
|---|---|---|
| EP | 0256055 | 2/1988 |
| EP | 0323997 | 7/1989 |
| EP | 0338841 | 10/1989 |
| EP | 0606046 | 7/1994 |
| EP | 0780386 | 6/1997 |
| EP | 0818442 | 1/1998 |
| EP | 0931788 | 7/1999 |
| EP | 1004578 | 5/2000 |
| WO | WO 9005719 | 5/1990 |
| WO | WO 9109967 | 7/1991 |
| WO | WO 9110741 | 7/1991 |
| WO | WO 9117271 | 11/1991 |
| WO | WO 9201047 | 1/1992 |
| WO | WO 9202190 | 2/1992 |
| WO | WO 9209690 | 6/1992 |
| WO | WO 9215679 | 9/1992 |
| WO | WO 9218619 | 10/1992 |
| WO | WO 9220791 | 11/1992 |
| WO | WO 9301288 | 1/1993 |
| WO | WO 9306213 | 4/1993 |
| WO | WO 9317105 | 9/1993 |
| WO | WO 9402602 | 2/1994 |
| WO | WO 9519970 | 7/1995 |
| WO | WO 9521613 | 8/1995 |
| WO | WO 9627583 | 9/1996 |
| WO | WO 9633172 | 10/1996 |
| WO | WO 9633735 | 10/1996 |
| WO | WO 9634096 | 10/1996 |
| WO | WO 9713760 | 4/1997 |
| WO | WO 9722596 | 6/1997 |
| WO | WO 9732856 | 9/1997 |
| WO | WO 9802434 | 1/1998 |
| WO | WO 9802437 | 1/1998 |
| WO | WO 9802438 | 1/1998 |
| WO | WO 9803516 | 1/1998 |
| WO | WO 9807697 | 2/1998 |
| WO | WO 9814451 | 4/1998 |
| WO | WO 9816654 | 4/1998 |
| WO | WO 9824893 | 6/1998 |
| WO | WO 9830566 | 7/1998 |
| WO | WO 9833768 | 8/1998 |
| WO | WO 9834915 | 8/1998 |
| WO | WO 9834918 | 8/1998 |
| WO | WO 9850356 | 11/1998 |
| WO | WO 9850433 | 11/1998 |
| WO | WO 9854093 | 12/1998 |
| WO | WO 9907675 | 2/1999 |
| WO | WO 9910349 | 3/1999 |
| WO | WO 9916755 | 4/1999 |
| WO | WO 9924440 | 5/1999 |
| WO | WO 9929667 | 6/1999 |
| WO | WO 9935132 | 7/1999 |
| WO | WO 9935146 | 7/1999 |
| WO | WO 9945031 | 9/1999 |
| WO | WO 9952889 | 10/1999 |
| WO | WO 9952910 | 10/1999 |
| WO | WO 9953049 | 10/1999 |
| WO | WO 9960023 | 11/1999 |
| WO | WO 9961422 | 12/1999 |
| WO | WO 9962890 | 12/1999 |
| WO | WO 0009560 | 2/2000 |
| WO | WO 0037504 | 6/2000 |
| WO | WO0050067 | 8/2000 |
| WO | WO 0056772 | 9/2000 |
| WO | WO 02/053596 * | 7/2002 |
| WO | WO 02053596 | 7/2002 |
| WO | WO 03059951 | 7/2003 |
| WO | WO 03093317 | 11/2003 |
| WO | WO 03100008 | 12/2003 |
| WO | WO 03100059 | 12/2003 |
| WO | WO 03106621 | 12/2003 |
| WO | WO 2004071529 | 8/2004 |
| WO | WO 2004087756 | 10/2004 |

OTHER PUBLICATIONS

Drexhage, H.A. & Wulffraat, N.M., "Endocrine autoimmune diseases," Netherlands Journal of Medicine, 45:285-293 (1994).

Kim, Bhumsoo, et al., "Insulin receptor substrate 2 and she play different roles in insulin-like growth factor I signaling," Journal of Biological Chemistry, 273:34543-34550 (1998).

Smith, Lois E., et al., "Regulation of vascular endothelial growth factor-dependent retinal neovascularization by insulin-like growth factor-1 receptor," Nature Medicine, 5:1390-1395 (1999).

Tappy, Luc, et al., "Antibodies to insulin-like growth factor I receptors in diabetes and other disorders," Diabetes, 37:1708-1714 (1988).

Thompson, Kathleen, et al., "Low prevalence of autoantibodies to the insulin-like growth factor I receptor in children with short stature," Pediatric Research, 32:455-459 (1992).

Weightman, David R., et al., "Autoantibodies to IGF-1 binding sites in thyroid associated opthalmopathy," Autoimmunity, 16:251-257 (1993).

Wraight, Christopher, et al., "Reversal of epidermal hyperproliferation in psoriasis by insulin like growth factor I receptor antisense oligonucleotides," Nature Biotechnology, 18:521-526 (2000).

Altschul et al., "Basic local alignment search tool," *Journal of Molecular Biology*, 215(1):403 410(1990).

Altschul et al., "Gapped BLAST and PSI-BLAST: a new generation of protein database search programs," *Nucleic Acids Research*, 25(17):3389-402 (1997).

Arteaga et al., "Interference of the IGF system as a strategy to inhibit breast cancer growth," *Breast Cancer Research Treatment*, 22:101-106 (1992).

Arteaga et al., "Blockade of the type I somatomedin receptor inhibits growth of human breast cancer cells in athymic mice," *Journal of Clinical Investigation*, 84:1418-1423 (1989).

Barbas et al., "Assembly of combinatorial antibody libraries on phage surfaces: the gene III site," *PNAS*, 88:7978-7982 (1991).

Barkan, "New options for diagnosing and treating acromegaly," *Cleveland Clinic Journal of Medicine*, 65(7):343-349 (1998).

Bayes-Genis et al., "The insulin-like growth factor axis. A review of atherosclerosis and restenosis," *Circulation Research*, 86(2):125-130 (2000).

Bird et al., "Single-chain antigen-binding proteins," *Science*, 242:423-426 (1988).

Bowie et al., "A method to identify protein sequences that fold into a known three-dimensional structure," *Science*, 253:164-170 (1991).

Butler et al., "Stimulation of tumor growth by recombinant human insulin-like growth factor-I (IGF-I) is dependent on the dose and the level of IGF-I receptor expression," *Cancer Research*, 58:3021-3027 (1998).

Chothia et al., "Canonical structures for the hypervariable regions of immunoglobulins," *Journal of Molecular Biology*, 196:901-917 (1987).

Chothia et al, "Conformations of immunoglobulin hypervariable regions," *Nature*, 342:877-883 (1989).

Clackson et al., "Making antibody fragments using phage display libraries," *Nature*, 352:624 628(1991).

Coleman P.M., Effect of amino acid sequence changes on antibody-antigen interactions, Research in Immunology, 145:33-36, 1994.

Cullen et al., "Insulin-like growth factor receptor expression and function in human breast cancer," *Cancer Research*, 50: 48-53 (1990).

Cullen et al., "Glutathione S-transferase n amplification is associated with cisplatin resistance in head and neck squamous cell carcinoma cell lines and primary tumors," *Cancer Research*, 63: 8097-8102 (2003).

D'Ambrosio et al., A soluble insulin-like growth factor I receptor that induces apoptosis of tumor cells in vivo and inhibits tumorigenesis, *Cancer Research*, 56:4013-4020 (1996).

Du Pasquier, "Evolution of the immune system," *Fundamental Immunology, Second Edition*, edited by William E. Paul, Raven Press Ltd., NY, 139-165 (1989).

Evans et al., "Design of nonpeptidal ligands for a peptide receptor: cholecystokinin antagonists," *Journal of Medicinal Chemistry*, 30:1229-1239 (1987).

Fagerstam et al., "Detection of antigen-antibody interactions by surface plasmon resonance. Applications to epitope mapping," *Journal of Molecular Recognition*, 3:(5,6):208-214 (1990).

Fanger et al., "Production and use of anti-FcR bispecific antibodies,"*Immunomethods*,.4:72-81 (1994).

Fauchere, "Elements for the rational drug design of peptides drugs," *Advances in Drug Research*, 15:29-69 (1986).

Foekens et al., "Prognostic value of receptors for insulin-like growth factor 1, somatostatin, and epidermal growth factor in human breast cancer," *Cancer Research*, 49:7002-7009 (1989).

Freed et al., "Insulin-like growth factor-I and its autocrine role in growth of MCF-7 human breast cancer cells in culture," *Journal of Molecular Endocrinology*, 3:183-189 (1989).

Fuchs et al., "Targeting recombinant antibodies to the surface of *Escherichia coli*: fusion to a peptidoglycan associated lipoprotein," *Biotechnology*, 9:1369-1372 (1991).

Galfre et al., "Preparation of monoclonal antibodies: strategies and procedures," *Methods in Enzymology*, 73:3-46 (1981).

Garrad et al., "$F_AB$ assembly and enrichment in a monovalent phage display system," *Biotechnology*, 9:1373-1377 (1991).

Geran, et al., "Protocols for screening chemical agents and natural products against animal tumors and other biological systems," *Cancer Chemotherapy Reports*, 3(2):1-104 (1972).

Goldring et al., "Cytokines and cell growth control," *Critical Reviews in Eukaryotic Gene Expression*, 1:31-326 (1991).

Gonnet et al., "Exhaustive matching of the entire protein sequence database," *Science*, 256:1443-1445 (1992).

Gram et al., "In vitro selection and affinity maturation of antibodies from a naive combinatorial immunoglobulin library," *PNAS*, 89:3576-3580 (1992).

Green et al., "Antigen-specific human monoclonal antibodies from mice engineered with human Ig heavy and light chain YACs," *Nature Genetics*, 7:13-21 (1994).

Green et al., "Regulation of B cell development by variable gene complexity in mice reconstituted with human immunoglobulin yeast artificial chromosomes," *Journal of Experimental Medicine*, 188(3):483-495 (1998).

Griffiths et al., "Human anti-self antibodies with high specificity from phage display libraries," *The EMBO Journal*, 12(2):725-734 (1993).

Grimberg et al., "Role of insulin-like growth factors and their binding proteins in growth control and carcinogenesis," *Journal of Cellular Physiology*, 183:1-9 (2000).

Guo et al., "Characterization of insulinlike growth factor I receptors in human colon cancer," *Gastroenterology*, 102(4):1101-1108 (1992).

Harrington et al., "c-Myc-induced apoptosis in fibroblasts is inhibited by specific cytokines," *The EMBO Journal*, 13(14):3286-3295 (1994).

Hawkins et al., "Selection of phage antibodies by binding affinity mimicking affinity maturation," *Journal of Molecular Biology*, 226:889-896 (1992).

Hay et al., "Bacteriophage cloning and *Escherichia coli* expression of a human IgM Fab." *Hum. Antibod. Hybridomas*, 3:81-85 (1992).

Hockenbery et al., "Bcl-2 is an inner mitochondrial membrane protein that blocks programmed cell death," *Nature*, 348:334-336 (1990).

Holliger et al., "Diabodies: small bivalent and bispecific antibody fragments," *PNAS*, 90:6444 6448(1993).

Hoogenboom et al., "Multi-subunit proteins on the surface of filamentous phage: methodologies for displaying antibody (Fab) heavy and light chains," *Nucleic Acids Research*, 19(15):4133-4137 (1991).

Huse et al., "Generation of a large combinatorial library of the immunoglobulin repertoire in phage lambda," *Science*, 246:1275-1281 (1989).

Huston et al., "Protein engineering of antibody binding sites: recovery of specific activity in an anti-digoxin single-chain Fv analogue produced in *Escherichia coli*," *PNAS*, 85:5879-5883_(1988).

Ill et al., "Design and construction of a hybrid immunoglobulin domain with properties of both heavy and light chain variable regions," *Protein Engineering*, 10(8): 949-957 (1997).

Jiang et al., "Induction of tumor suppression and glandular differentiation of A549 lung carcinoma cells by dominant-negative IGF-1 receptor," *Oncogene*, 18:6071-6077 (1999).

Johnsson et al., "Comparison of methods for immobilization to carboxymethyl dextran sensor surfaces by analysis of the specific activity of monoclonal antibodies," *Journal of Molecular Recognition*, 8:125-131 (1995).

Johnsson et al., "Immobolization of proteins to a carboxymethyldextran-modified gold surface for biospecific interaction analysis in surface plasmon resonance sensors," *Analytical Biochemistry*, 198:268-277 (1991).

Jonsson et al., "Introducing a biosensor based technology for real-time biospecific interaction analysis," *Ann. Biologie Clinique.*, 51:19-26 (1993).

Jonsson et al., "Real-time biospecific interaction analysis using surface plasmon resonance and a sensor chip technology," *BioTechniques*, 11(5):620-627 (1991.

Kaiser et al., "Expression of insulin-like growth factor receptors I and II in normal human lung and in lung cancer," *Journal of Cancer Research and Clinical Oncology*, 119(11):665-668 (1993).

Kalebic et al., "In vivo treatment with antibody against IGF-I receptor suppresses growth of human rhabdomyosarcoma and down-regulates $p34^{cdc2}$," *Cancer Research*, 54:5531-5534 (19.94.

Kim et al., "Insulin receptor substrate 2 and She play different roles in insulin-like growth factor I signaling," *Journal of Biological Chemistry*, 273:34543-34550 (1998).

Lane, "A death in the life of p53," *Nature*, 362:786-787 (1993).

LaPlanche et al., "Phosphorothiolate-modified oligodeoxyribonucleotides, III. NMR and UV spectroscopic studies of the Rp Rp, Sp Sp, and Rp-Sp duplexes, [d(GG5AATTCC)]2, derived from diastereomeric O-ethyl phosphorothioates," *Nucleic Acids Research*, 14(22):9081-9093 (1986).

Laron, "Clinical use of somatomedin-1," *Pediatric Drugs*, 1(3):155-159 (1999).

LeRoith et al., "Molecular and cellular aspects of the insulin-like growth factor I receptor," *Endocrine Reviews*, 16(2):143-163 (1995).

Li et al., "Mitogenicity and transforming activity of the insulin-like growth factor-I receptor with mutations in the tyrosine kinase domain," *Journal of Biological Chemistry*, 269:32558 32564(1994).

Macaulay, "Insulin-like growth factors and cancer," *British Journal of Cancer*, 65:311-320 (1992).

Macauley et al., "Autocrine function for insulin-like growth factor 1 in human small cell lung cancer cell lines and fresh tumor cells," *Cancer Research*, 50:2511-2517 (1990).

Martin et al, "The affinity-selection of a minibody polypeptide inhibitor of human interleukin 6," *The EMBO Journal*, 13(22): 5303-5309 (1994).

McCafferty et al., "Phage antibodies: filamentous phage displaying antibody variable domains," *Nature*, 348:552-554 (1990).

McDonnell et al., "bcl-2-immunoglobulin transgenic mice demonstrate extended B cell survival and follicular lymphoproliferation," *Cell*, 57:79-88 (1989).

Mendez et al., "Functional transplant of megabase human immunoglobulin loci recapitulates human antibody response in mice," *Nature Genetics*, 15:146-156 (1997).

Moody et al., "Growth factor and peptide receptors in small cell lung cancer," *Life Sciences*, 52:1161-1173 (1993).

Moyer et al., "Induction of apoptosis and cell cycle arrest by CP-358,774, an inhibitor of epidermal growth factor receptor tyrosine kinase," *Cancer Research*, 57:4838-4848 (1997).

Nakanishi et al., "Insulin-like growth factor-I can mediate autocrine proliferation of human small cell lung cancer cell lines in vitro," *Journal of Clinical Investigation*, 82:354-359 (1988).

Pearson, "Empirical statistical estimates for sequence similarity searches," *Journal of Molecular Biology*, 276:71-84 (1998).

Pearson, "Rapid and sensitive sequence comparison with FASTP and FASTA," *Methods in Enzymolology*, 183:63-98 (1990).

Pearson, "Flexible sequence similarity searching with the FASTA3 program package," *Methods in Molecular Biology*, 132:185-219 (2000).

Pearson, "Using the FASTA program to search protein and DNA sequence databases," *Methods in Molecular Biology*, 24:307-331 (1994).

Pearson, "Effective protein sequence comparison," *Methods in Enzymology*, 266:227-258 (1996).

Pietrzkowski et al., "Constitutive expression of insulin-like growth factor 1 and insulin-like growth factor 1 receptor abrogates all requirements for exogenous growth factors," *Cell Growth & Differentiation*, 3:199-205 (1992).

Pietrzkowski et al., "Roles of insullike growth factor 1 (IGF-1) and the IGF-1 receptor in epidermal growth factor-stimulated growth of 3T3 cells," *Molecular and Cellular Biology*, 12(9):3883-3889 (1992).
Poljak, "Production and structure of diabodies," *Structure*, 2:1121-1123 (1994).
Pollack et al., "Inhibition of epidermal growth factor receptor-associated tyrosine phosphorylation in human carcinomas with CP-358,774: Dynamics of receptor inhibition in situ and antitumor effects in athymic mice," *Journal of Pharmacology and Experimental Therapeutics*, 291(2):739-748 (1999).
Pollak et al., "Presence of somatomedin receptors on primary human breast and colon carcinomas," *Cancer Letters*, 38:223-230 (1987).
Prager et al., "Dominant negative inhibition of tumorigenesis in vivo by human insulin-like growth factor I receptor mutant," *PNAS*, 91:2181-2185 (1994).
Remacle-Bonnet et al., "Expression of Type I, but not Type II insulin-like growth factor receptor on both undifferentiated and differentiated HT29 human colon carcinoma cell line," *Journal of Clinical Endocrinology and Metabolism*, 75(2):609-616 (1992).
Resnicoff et al., "The insulin-like growth factor I receptor protects tumor cells from Apoptosis in vivo," *Cancer Research*, 55:2463-2469 (1995).
Resnicoff et al., "Correlation between apoptosis, tumorigenesis, and levels of insulin-like growth factor I receptors," *Cancer Research*, 55:3739-3741 (1995).
Rizo et al., "Constrained peptides: models of bioactive peptides and protein substructures," *Annual Review of Biochemistry*, 61:387-418 (1992).
Rodriguez-Tarduchy et al., "Insulin-like growth factor-I inhibits apoptosis in IL-3-dependent hemopoietic cells," *Journal of Immunology*, 149(2):535-540 (1992).
Rosen et al., "Circulating IGF-I: new perspectives for a new century," *Trends in EndocrinologyMetabolism*, 10(4):136-141 (1999).
Sandberg-Nordqvist et al., "Characterization of insulin-like growth factor 1 in human primary brain tumors," *Cancer Research*, 53:2475-2478 (1993).
Sell et al., "Insulin-like growth factor 1 (IGF-1) and the IGF-1 receptor prevent etoposide induced apoptosis," *Cancer Research*, 55:303-306 (1995).
Smith et al., "Regulation of vascular endothelial growth factor-dependent retinal neovascularization by insulin-like growth factor-1 receptor," *Nature Medicine*, 5(12): 1390 1395(1999).
Stec et al., "Automated solid-phase synthesis, separation, and stereochemistry of phosphorothioate analogues of oligodeoxyribonucleotides," *Journal of the American Chemical Society*, 106(20):6077-6079 (1984).
Stein et al., "Physiochemical properties of phosphorothioate oligodeoxynucleotides," *Nucleic Acids Research*, 16(8):3209-3221 (1988).
Thornton et al., "Prediction of progress at last," *Nature*, 354(14):105-106 (1991).
Traunecker et al., "Bispecific single chain molecules (Janusins) target cytotoxic lymphocytes on HIV infected cells," *The EMBO Journal*, 10(12):3655-3659 (1991).
Traunecker et al., "Janusin: new molecular design for bispecific reagents," *International Journal of Cancer*, 7:51-52 (1992).
Trojan et al., "Treatment and prevention of rat glioblastoma by immunogenic C6 cells expressing antisense insulin-like growth factor 1 RNA," *Science*, 259:94-97 (1993).
Uhlmann et al., "Antisense oligonucleotides: a new therapeutic principle," *Chemical Reviews*, 90(4):543-584 (1990).
Ullrich et al., "Signal transduction by receptors with tyrosine kinase activity," *Cell*, 61:203-212 (1990).
Ullrich et al., "Insulin-like growth factor I receptor primary structure: comparison with insulin receptor suggests structural determinants that define functional specificity," *The EMBO Journal*, 5(10):2503-2512 (1986).
Veber et al., "The design of metabolically-stable peptide analogs," *TINS*, 8(9):392-396 (1985).

Ward et al., "Binding activities of a repertoire of single immunoglobulin variable domains secreted from *Escherichia coli*," *Nature*, 341:544-546 (1989).
Williams, "Programmed cell death: apoptosis and oncogenesis," *Cell*, 65:1097-1098 (1991).
Winter et al., "Humanized antibodies," *Immunology Today*, 14(6):243-246 (1993).
Wright et al., "Genetically engineered antibodies: progress and prospects," *Critical Reviews in Immunology*, 12:(3,4)125-168 (1992).
Yee et al., "Analysis of insulin-like growth factor I gene expression in malignancy: evidence for a paracrine role in human breast cancer" *Molecular Endocrinology*, 3(3):509-517 (1989).
Yee et al., "Insulin-like growth factor II mRNA expression in human breast cancer," *Cancer Research*, 48:6691-6696 (1988).
Zon et al., "Phosphorothioate oligonucleotides," *Oligonucleotides and Analogues: A Practical Approach*, 87-108 (F. Eckstein, Ed., Oxford University Press, Oxford England (1991).
Zon et al., "Phosphorothioate oligonucleotides: chemistry, purification, analysis, scale-up and future directions," *Anti-Cancer Drug Design*, 6:539-568 (1991).
William E. Paul, Fundamental Immunology 242 M.D. ed., 3d ed. 1993.
Rudikoff et al., "Single amono acid substitutuion altering antigen-bindign specification", (Proc Natl Acad Sci USA 1982 vol. 79 p. 1979.
Groves et al., "Production of Ovine Monoclonal Antibody to Testosterone by an Interspecies Fusion," *Hybridoma* 6:71, 1987.
Rubini et al., Characterization of an Antibody that Can Detect and Activate IGF-1R Receptor Human Cancers, Experimental Cell Research 251:22-32, 1999.
Li, S.-L. et al., "Single-chain Antibodies Against Human Insulin-like Growth Factor I Receptor: Expression, Purification and Effect on Tumor Growth," *Cancer Immunology and Immunotherapy*, 49:243-252 (2000).
Hermanto, U. et al., "Inhibition of Mitogen-activated Protein Kinase Kinase Selectively Inhibits Cell Proliferation in Human Breast Cancer Cells Displaying Enhanced Insulin-like Growth Factor 1-mediated Mitogen-activated Protein Kinase Activation," *Cell Growth & Differentiation*, 11:655-664 (2000).
Mitsiades, C., et al., The IGF/IGF-1R system is a major therapeutic target for multiple myeloma, other hematologic malignancies and solid tumors, Blood, vol. 100, No. 11, Nov. 16, 2004 p. 170A, XP002293672, abstract.
Mitsiades, C., et al., Gene expression and proteomic profiling of multiple myeloma (MM) cells co-cultured with bone marrow (BM) stromal cells or stimulated with BM-derived cytokines: Implications for therapeutic targeting of the BM milieu in MM, Blood, vol. 100, No. 11, 2002, p. 811A, XP002293673, abstract.
Elagiab, K., et al., Immunoglobulin variable genes and epitope recognition of human monoclonal anti-Ro 52-kd in primary Sjogren's syndrome, Arthritis and Rheumatism, vol. 42, No. 11, Nov. 1999, pp. 2471-2481, XP002293674, abstract.
Aburatani, T., et al, Importance of CDR H3 basal residue in VH/VL interaction of human antibodies, Journal of Biochemistry, vol. 132, No. 5, Nov. 2002, pp. 775-782, XP002293675.
Hailey, J., et al., Neutralizing anti-insulin-like growth factor receptor 1 antibodies inhibit receptor function and induce receptor degradation in tumor cells, Molecular Cancer Therapeutics, vol. 1, 2002, pp. 2002-20012.
Steele-Perkins, G., et al., Expression and characterization of a functional human insulin-like growth factor I receptor, The Journal of Biological Chemistry, vol. 263, No. 23, 1988, pp. 11486-11492.
Rohlik, Q., et al., An antibody to the receptor for insulin-like growth factor I tissue culture, Biochemical and Biophysical Research, vol. 149, No. 1.
Vaughan, T., et al., Human antibodies with sub-namolar affinities isolated from a large non-immunized phage display library, Nature Biotechnology, vol. 14, 1996, pp. 309-314.

* cited by examiner

FIG. 1A

```
2.13.2K    GACATCCAGA TGACCCAGTT TCCATCCTCC CTGTCTGCAT CTGTAGGAGA  50
A30        GACATCCAGA TGACCCAGTC TCCATCCTCC CTGTCTGCAT CTGTAGGAGA  50
2.14.3k    ---------- ---------- ----TCCTCC CTGTCTGCAT CTGTAGGAGA  26
2.12.1k    ---------- ---------- ---------- -----TGCAT CTGTAGGAGA  15
4.9.2k     GACATCCAGA TGACCCAGTC TCCATCCTCC CTGTCTGCAT CTGTAGGAGA  50
Consensus  GACATCCAGA TGACCCAGTY TCCATCCTCC CTGTCTGCAT CTGTAGGAGA  50
                                                    CDR1

2.13.2K    CAGAGTCACC ATCACTTGCC GGGCAAGTCA GGGCATTAGA AATGATTTAG  100
A30        CAGAGTCACC ATCACTTGCC GGGCAAGTCA GGGCATTAGA AATGATTTAG  100
2.14.3k    CAGAGTCACC TTCACTTGCC GGGCAAGTCA GGACATTAGA CGTGATTTAG   76
2.12.1k    CAGAGTCACC TTCACTTGCC GGGCAAGTCA GGACATTAGA CGTGATTTAG   65
4.9.2k     CAGAGTCACC ATCACTTGCC GGGCAAGTCA GGGCATTAGA AGTGATTTAG  100
Consensus  CAGAGTCACC WTCACTTGCC GGGCAAGTCA GGRCATTAGA MRTGATTTAG  100

2.13.2K    GCTGGTATCA GCAGAAACCA GGGAAAGCCC CTAAGCGCCT GATCTATGCT  150
A30        GCTGGTATCA GCAGAAACCA GGGAAAGCCC CTAAGCGCCT GATCTATGCT  150
2.14.3k    GCTGGTATCA GCAGAAACCA GGGAAAGCTC CTAAGCGCCT GATCTATGCT  126
2.12.1k    GCTGGTATCA GCAGAAACCA GGGAAAGCTC CTAAGCGCCT GATCTATGCT  115
4.9.2k     GCTGGTTTCA GCAGAAACCA GGGAAAGCCC CTAAGCGCCT GATCTATGCT  150
Consensus  GCTGGTWTCA GCAGAAACCA GGGAAAGCYC CTAAGCGCCT GATCTATGCT  150
                CDR2

2.13.2K    GCATCCCGTT TGCACAGAGG GGTCCCATCA AGGTTCAGCG GCAGTGGATC  200
A30        GCATCCAGTT TGCAAAGTGG GGTCCCATCA AGGTTCAGCG GCAGTGGATC  200
2.14.3k    GCATCCCGTT TACAAAGTGG GGTCCCATCA AGGTTCAGCG GCAGTGGATC  176
2.12.1k    GCATCCCGTT TACAAAGTGG GGTCCCATCA AGGTTCAGCG GCAGTGGATC  165
4.9.2k     GCATCCAAAT TACACCGTGG GGTCCCATCA AGGTTCAGCG GCAGTGGATC  200
Consensus  GCATCCMRWT TRCAMMGWGG GGTCCCATCA AGGTTCAGCG GCAGTGGATC  200

2.13.2K    TGGGACAGAA TTCACTCTCA CAATCAGCAG CCTGCAGCCT GAAGATTTTG  250
A30        TGGGACAGAA TTCACTCTCA CAATCAGCAG CCTGCAGCCT GAAGATTTTG  250
2.14.3k    TGGGACAGAA TTCACTCTCA CAATCAGCAG CCTGCAGCCT GAAGATTTTG  226
2.12.1k    TGGGACAGAA TTCACTCTCA CAATCAGCAG CCTGCAGCCT GAAGATTTTG  215
4.9.2k     TGGGACAGAA TTCACTCTCA CAATCAGCCG CCTGCAGCCT GAAGATTTTG  250
Consensus  TGGGACAGAA TTCACTCTCA CAATCAGCMG CCTGCAGCCT GAAGATTTTG  250
                                        CDR3

2.13.2K    CAACTTATTA CTGTTTACAA CATAATAGTT ACCCGTGCAG TTTTGGCCAG  300
A30        CAACTTATTA CTGTCTACAG CATAATAGTT ACCC-TCCN- ----------  288
2.14.3k    CAACTTATTA CTGTCTACAG CATAATAATT ATCCTCGGAC GTTCGGCCAA  276
2.12.1k    CAACTTATTA CTGTCTACAG CATAATAATT ATCCTCGGAC GTTCGGCCAA  265
4.9.2k     CAACTTATTA CTGTCTACAG CATAATAGTT ACCCTCGGAC TTTCGGCGGA  300
Consensus  CAACTTATTA CTGTYTACAR CATAATARTT AYCCKYBSNS KTTYGGCSRR  300

2.13.2K    GGGACCAAGC TGGAGATCAA AC----                            322
A30        ---------- ---------- ------                            288
2.14.3k    GGGACCAAGC TGGAAATCAT ACGAAC                            302
2.12.1k    GGGACCAAGC TGGAAATCAT ACGAAC                            291
4.9.2k     GGGACCAAGC TGGAGATCAA AC----                            322
Consensus  GGGACCRAGS TGGARATCAW ACGAAC                            326
```

FIG. 1B

```
                                                                                    AGGAGA        7
4.17.3K    ---------- ---------- ---------- ---------- ---------- ----AGGAGA       50
012        GACATCCAGA TGACCCAGTC TCCATCCTCC CTGTCTGCAT CTGTAGGAGA                  50
Consensus  GACATCCAGA TGACCCAGTC TCCATCCTCC CTGTCTGCAT CTGYAGGAGA
                                                              CDR1

4.17.3K    CAGAGTCACC ATCACTTGCC GGGCAAGTCA GAGCATTAGT ACCTTTTTAA                  57
012        CAGAGTCACC ATCACTTGCC GGGCAAGTCA GAGCATTAGC AGCTATTTAA                 100
Consensus  CAGAGTCACC ATCACTTGCC GGGCAAGTCA GAGCATTAGY ASCTWTTTAA                 100

4.17.3K    ATTGGTATCA GCAGAAACCA GGGAAAGCCC CTAAACTCCT GATCCATGTT                 107
012        ATTGGTATCA GCAGAAACCA GGGAAAGCCC CTAAGCTCCT GATCTATGCT                 150
Consensus  ATTGGTATCA GCAGAAACCA GGGAAAGCCC CTAARCTCCT GATCYATGYT                 150
                CDR2

4.17.3K    GCATCCAGTT TACAAGTGG GGTCCCATCA AGGTTCAGTG GCAGTGGATC                   157
012        GCATCCAGTT TGCAAAGTGG GGTCCCATCA AGGTTCAGTG GCAGTGGATC                 200
Consensus  GCATCCAGTT TRCAARGTGG GGTCCCATCA AGGTTCAGTG GCAGTGGATC                 200

4.17.3K    TGGGACAGAT TTCACTCTCA CCATCAGCAG TCTGCAACCT GAAGATTTTG                  207
012        TGGGACAGAT TTCACTCTCA CCATCAGCAG TCTGCAACCT GAAGATTTTG                 250
Consensus  TGGGACAGAT TTCACTCTCA CCATCAGCAG TCTGCAACCT GAAGATTTTG                 250

4.17.3K    CAACTTACTA CTGTCAACAG AGTTACAATG CCCCACTCAC TTTCGGCGGA                  257
012        CAACTTACTA CTGTCAACAG AGTTACAGTA CCCC-TCCH- ----------                 288
Consensus  CAACTTACTA CTGTCAACAG AGTTACARTR CCCCAYCHC TTTCGGCGGA                  300
                                            CDR3

4.17.3K    GGGACCAAGG TGGAGATCAA AC                                               279
012        ---------- ---------- --                                               288
Consensus  GGGACCAAGG TGGAGATCAA AC                                               322
```

FIG. 1C

```
              |---------- ---------- ---------- ---------- ----------|
6.1.1K        |---------- ---------- ---------- ---------- ----------|   50
A27           GAAATTGTGT TGACGCAGTC TCCAGGCACC CTGTCTTTGT GTCCAGGGGA    50
Consensus     GAAATTGTGT TGACGCAGTC TCCAGGCACC CTGTCTTTGT GTCCAGGGGA
                                                          CDR1
                                                          ┌─────────
6.1.1K        -AGAGCCACC CTCTCCTGTA GGGCCAGTCA GAGTGTTCGC  GGCAGGTACT   49
A27           AAGAGCCACC CTCTCCTGCA GGGCCAGTCA GAGTGTTAGC  AGCAGCTACT  100
Consensus     AAGAGCCACC CTCTCCTGYA GGGCCAGTCA GAGTGTTMGC  RGCAGSTACT  100

6.1.1K        TAGCCTGGTA CCAGCAGAAA CCTGGCCAGG CTCCCCAGGCT CCTCATCTAT   99
A27           TAGCCTGGTA CCAGCAGAAA CCTGGCCAGG CTCCCCAGGCT CCTCATCTAT  150
Consensus     TAGCCTGGTA CCAGCAGAAA CCTGGCCAGG CTCCCCAGGCT CCTCATCTAT  150
                    CDR2
              └─────────

6.1.1K        GGTGCATCCA GCAGGGCCAC TGGCATCCCA GACAGGTTCA GTGGCAGTGG   149
A27           GGTGCATCCA GCAGGGCCAC TGGCATCCCA GACAGGTTCA GTGGCAGTGG   200
Consensus     GGTGCATCCA GCAGGGCCAC TGGCATCCCA GACAGGTTCA GTGGCAGTGG   200

6.1.1K        GTCTGGGACA GACTTCACTC TCACCATCAG CAGACTGGAG CCTGAAGATT   199
A27           GTCTGGGACA GACTTCACTC TCACCATCAG CAGACTGGAG CCTGAAGATT   250
Consensus     GTCTGGGACA GACTTCACTC TCACCATCAG CAGACTGGAG CCTGAAGATT   250
                                                          CDR3
                                                          ┌─────────
6.1.1K        TTACTGTCAG CAGTATGGTA GTTCACCTCG NACGTTCGGC              249
A27           TTACTGTCAG CAGTATGGTA GCTCACCTCC ----------              288
Consensus     TTACTGTCAG CAGTATGGTA GYTCACCTCS NACGTTCGGC              300

6.1.1K        CAAGGGACCA AGGTGGAAAT CAAAC                              274
A27           ---------- ---------- -----                              290
Consensus     CAAGGGACCA AGGTGGAAAT CAAAC                              325
```

FIG. 2A

```
2.12.1H     ---------- ---------- ---GGGAGGC TTGGTCAAGC CTGGA-GGTC    26
DP35        CAGGTGCAGC TGGTGGAGTC TGGGGGAGGC TTGGTCAAGC CTGGAGGGTC     50
Consensus   CAGGTGCAGC TGGTGGAGTC TGGGGGAGGC TTGGTCAAGC CTGGAGGGTC     50
                                                            CDR1
2.12.1H     CCTGAGACTC TCCTGTGCAG CCTCTGGATT CACTTTCAGT GACTACTATA    76
DP35        CCTGAGACTC TCCTGTGCAG CCTCTGGATT CACCTTCAGT GACTACTACA   100
Consensus   CCTGAGACTC TCCTGTGCAG CCTCTGGATT CACYTTCAGT GACTACTAYA   100

2.12.1H     TGAGCTGGAT CCGCCAGGCT CCAGGGAAGG GGCTGGAATG GGTTTCATAC    126
DP35        TGAGCTGGAT CCGCCAGGCT CCAGGGAAGG GGCTGGAGTG GGTTTCATAC    150
Consensus   TGAGCTGGAT CCGCCAGGCT CCAGGGAAGG GGCTGGARTG GGTTTCATAC    150
                                                 CDR2
2.12.1H     ATTAGTAGTA GTGGTAGTAC CAGACTAC GCAGACTCTG TGAAGGGCCG      176
DP35        ATTAGTAGTA GTGGTAGTAC CATATACTCT GCAGACTCTG TGAAGGGCCG    200
Consensus   ATTAGTAGTA GTGGTAGTAC CAKAKACTCT GCAGACTCTG TGAAGGGCCG    200

2.12.1H     ATTCACCATC TCCAGGGACA ACGCCAAGAA CTCACTGTAT CTGCAAATGA    226
DP35        ATTCACCATC TCCAGGGACA ACGCCAAGAA CTCACTGTAT CTGCAAATGA    250
Consensus   ATTCACCATC TCCAGGGACA ACGCCAAGAA CTCACTGTAT CTGCAAATGA    250

2.12.1H     ACAGCCTGAG AGCCGAGGAC ACGGCCGTGT ATTACTGTGT GAGAGATGGA    276
DP35        ACAGCCTGAG AGCCGAGGAC ACGGCCGTGT ATTACTGTGC GAGAGA-----   296
Consensus   ACAGCCTGAG AGCCGAGGAC ACGGCCGTGT ATTACTGTGY GAGAGATGGA    300
                                                CDR3
2.12.1H     GTGGAAACTA CTTTTTACTA CTACTACTAC GGTATGGACG TCGGGGCCA    326
DP35        ---------- ---------- ---------- ---------- ---------    296
Consensus   GTGGAAACTA CTTTTTACTA CTACTACTAC GGTATGGACG TCGGGGCCA    350

2.12.1H     AGGGACCACG GTCACCGTCT CCTCAG                              352
DP35        ---------- ---------- ------                              296
Consensus   AGGGACCACG GTCACCGTCT CCTCAG                              376
```

FIG. 2B

```
PF2-2.14.3H.DNA   ------------ ------------ GGGCCCAGGA CTGGTGAAGC CTTCGGAGAC      30
VIV-4/4.35        CAGGTGCAGC TGCAGGAGTC GGGCCCAGGA CTGGTGAAGC CTTCGGAGAC          50
Consensus         CAGGTGCAGC TGCAGGAGTC GGGCCCAGGA CTGGTGAAGC CTTCGGAGAC          50

PF2-2.14.3H.DNA   CCTGTCCCTC ACCTGCACTG TCTCTGGTGG CTCCATCAGT AATTACTACT          80
VIV-4/4.35        CCTGTCCCTC ACCTGCACTG TCTCTGGTGG CTCCATCAGT AGTTACTACT         100
Consensus         CCTGTCCCTC ACCTGCACTG TCTCTGGTGG CTCCATCAGT ARTTACTACT         100
                                                                  CDR1

PF2-2.14.3H.DNA   GGAGCTGGAT CCGGCAGCCC GCCGGGAAGG GACTGGAGTG GATTGGGCGT         130
VIV-4/4.35        GGAGCTGGAT CCGGCAGCCC GCCGGGAAGG GACTGGAGTG GATTGGGCGT         150
Consensus         GGAGCTGGAT CCGGCAGCCC GCCGGGAAGG GACTGGAGTG GATTGGGCGT         150

PF2-2.14.3H.DNA   ATCTATATCCA GTGGGGAGCC CCCTCCCCTCA AGAGTCGAGT                   180
VIV-4/4.35        ATCTATATCCA GTGGGGAGCAC CCCTCCCCTCA AGAGTCGAGT                  200
Consensus         ATCTATATCCA GTGGGGAGCMC CCCTCCCCTCA AGAGTCGAGT                  200
                          CDR2

PF2-2.14.3H.DNA   CACCATGTCA GTAGACACGT CCAAGAACCA GTTCTCCCTG AAGCTGAACT         230
VIV-4/4.35        CACCATGTCA GTAGACACGT CCAAGAACCA GTTCTCCCTG AAGCTGAGCT         250
Consensus         CACCATGTCA GTAGACACGT CCAAGAACCA GTTCTCCCTG AAGCTGARCT         250

PF2-2.14.3H.DNA   CTGTGACCGC CGCGGACACG GCCGTGTATT ACTGTGCGGT AACGATTTTT         280
VIV-4/4.35        CTGTGACCGC CGCGGACACG GCCGTGTATT ACTGTGCGG- ---------           288
Consensus         CTGTGACCGC CGCGGACACG GCCGTGTATT ACTGTGCGGT AACGATTTTT         300
                          CDR3

PF2-2.14.3H.DNA   GGAGTGGTTA TTATCTTTGA CTACTGGGGC CAGGGAACCC TGGTCACCGT         330
VIV-4/4.35        ---------- ---------- ---------- -AGAGAB--- ---------           294
Consensus         GGAGTGGTTA TTATCTTTGA CTACTGGGGC CAGRGAACCC TGGTCACCGT         350

PF2-2.14.3H.DNA   CTCCTCAG                                                       338
VIV-4/4.35        --------                                                       294
Consensus         CTCCTCAG                                                       358
```

FIG. 2C-1

```
6.1.1H     GAGGTGCAGC TGTTGGAGTC TGGGGGAGGC TTGGTACAGC CTGGGGGGTC  50
4.9.2H     GAGGTGCAGC TGTTGGAGTC TGGGGGAGGC TTGGTACAGC CTGGGGGGTC  50
DP47       GAGGTGCAGC TGTTGGAGTC TGGGGGAGGC TTGGTACAGC CTGGGGGGTC  50
2.13.2H    GAGGTGCAGC TGTTGGAGTC TGGGGGAGGC TTGGTACAGC CTGGGGGGTC  50
Consensus  GAGGTGCAGC TGTTGGAGTC TGGGGGAGGC TTGGTACAGC CTGGGGGGTC  50
                                                            CDR1

6.1.1H     CCTGAGACTC TCCTGTGCAG CCTCTGGATT CACCTTTAGC AGCTATGCCA 100
4.9.2H     CCTGAGACTC TCCTGTGCAG CCTCTGGATT CACCTTTAGC AGCTATGCCA 100
DP47       CCTGAGACTC TCCTGTGCAG CCTCTGGATT CACCTTTAGC AGCTATGCCA 100
2.13.2H    CCTGAGACTC TCCTGTACAG CCTCTGGATT CACCTTTAGC AGCTATGCCA 100
Consensus  CCTGAGACTC TCCTGTRCAG CCTCTGGATT CACCTTTAGC AGCTATGCCA 100
               CDR1                                          CDR2

6.1.1H     TGAGCTGGGT CCGCCAGGCT CCAGGGAAGG GGCTGGAGTC GGTCTCAGGT 150
4.9.2H     TGAGCTGGGT CCGCCAGGCT CCAGGGAAGG GGCTGGAGTC GGTCTCAGCT 150
DP47       TGAGCTGGGT CCGCCAGGCT CCAGGGAAGG GGCTGGAGTC GGTCTCAGCT 150
2.13.2H    TGAACTGGGT CCGCCAGGCT CCAGGGAAGG GGCTGGAGTC GGTCTCAGST 150
Consensus  TGARCTGGGT CCGCCAGGCT CCAGGGAAGG GGCTGGAGTC GGTCTCAGST 150
                                CDR2

6.1.1H     ATTACTGGGA GTGGTGGTAG TACATACTAC GCAGACTCCG TGAAGGGCCG 200
4.9.2H     ATTAGTGGTA GTGGTGGTAT CACATACTAC GCAGACTCCG TGAAGGGCCG 200
DP47       ATTAGTGGTA GTGGTGGTAG CACATACTAC GCAGACTCCG TGAAGGGCCG 200
2.13.2H    ATTAGTGGTA GTGGTGGTAC CACATTCTAC GCAGACTCCG TGAAGGGCCG 200
Consensus  ATTASTGGKA GTGGTGGTAB YACATWCTAC GCAGACTCCG TGAAGGGCCG 200

6.1.1H     GTTCACCATC TCCAGAGACA ATTCCAAGAA CACGCTGTAT CTGCAAATGA 250
4.9.2H     GTTCACCATC TCCAGAGACA ATTCCAAGAA CACGCTGTAT CTGCAAATGA 250
DP47       GTTCACCATC TCCAGAGACA ATTCCAAGAA CACGCTGTAT CTGCAAATGA 250
2.13.2H    GTTCACCATC TCCAGAGACA ATTCCAGGAC CACGCTGTAT CTGCAAATGA 250
Consensus  GTTCACCATC TCCAGAGACA ATTCCARGAM CACGCTGTAT CTGCAAATGA 250
                                                             CDR3

6.1.1H     ACAGCCTGAG AGCCGAGGAC ACGGCCGTAT ATTACTGTGC GAAAGATC--  298
4.9.2H     ACAGCCTGAG AGCCGAGGAC ACGGCCGTAT ATTACTGTGC GAAAGATGTG 300
DP47       ACAGCCTGAG AGCCGAGGAC ACGGCCGTAT ATTACTGTGC GAAAGA----  296
2.13.2H    ACAGCCTGAG AGCCGAGGAC ACGGCCGTAT ATTACTGTGC GAAAGATCTT 300
Consensus  ACAGCCTGAG AGCCGAGGAC ACGGCCGTAT ATTACTGTGC GAAAGATCTK 300
                          CDR3-for 4.9.2 and 2.13.2

6.1.1H     ---------- ---------- ---------- ---------- --------C- 299
4.9.2H     GGCTACGGTG ACTTTTACTA CTACTACTAC GGTATGGACG TCTGGGGCCA 350
DP47       ---------- ---------- ---------- ---------- ----------  296
2.13.2H    GGCTACGGTG ACTTTTACTA CTACTACTAC GGTATGGACG TCTGGGGCCA 350
Consensus  GGCTACGGTG ACTTTTACTA CTACTACTAC GGTATGGACG TCTGGGGCCA 350
                   CDR3-for 6.1.1

6.1.1H     AGGGACTACG GTGATTATGA GTTGGTTCGA CCCCTGGGGC CAGGGAACCC 349
4.9.2H     AGGGACTAC- ---------- ---------- ---------- ----------  359
DP47       ---------- ---------- ---------- ---------- ----------  296
2.13.2H    AGGGACTAC- ---------- ---------- ---------- ----------  359
Consensus  AGGGACYACG GTGATTATGA GTTGGTTCGA CCCCTGGGGC CAGGGAACCC 400
```

FIG. 2C-2

```
6.1.1H     TGGTCACCGT CTCCTCAG                                     367
4.9.2H     -GGTCACCGT CTCCTCAG                                     376
DP47       ---------- --------                                     296
2.13.2H    -GGTCACCGT CTCCTCAG                                     376
Consensus  TGGTCACCGT CTCCTCAG                                     418
```

FIG. 2D

```
4.17.3H    ---------- ---------- ---CCCAGGA CTGGTGAAGC CTTCGGAGAC   27
DP71       CAGGTGCAGC TGCAGGAGTC GGGCCCAGGA CTGGTGAAGC CTTCGGAGAC   50
Consensus  CAGGTGCAGC TGCAGGAGTC GGGCCCAGGA CTGGTGAAGC CTTCGGAGAC   50
                                                           CDR1

4.17.3H    CCTGTCCCTC ACCTGCACTG TCTCTGGTGG CTCCATCAGT AGTTACTACT   77
DP71       CCTGTCCCTC ACCTGCACTG TCTCTGGTGG CTCCATCAGT AGTTACTACT  100
Consensus  CCTGTCCCTC ACCTGCACTG TCTCTGGTGG CTCCATCAGT AGTTACTACT  100
           CDR1

4.17.3H    GGAGTTGGAT CCGGCAGCCC CCAGGGAAGG GACTGGAGTG GATTGGGTAT  127
DP71       GGAGCTGGAT CCGGCAGCCC CCAGGGAAGG GACTGGAGTG GATTGGGTAT  150
Consensus  GGAGYTGGAT CCGGCAGCCC CCAGGGAAGG GACTGGAGTG GATTGGGTAT  150
                CDR2

4.17.3H    ATCTATTACA GTGGGAGCAC CAACTACAAC CCCTCCCTCA AGAGTCGAGT  177
DP71       ATCTATTACA GTGGGAGCAC CAACTACAAC CCCTCCCTCA AGAGTCGAGT  200
Consensus  ATCTATTACA GTGGGAGCAC CAACTACAAC CCCTCCCTCA AGAGTCGAGT  200

4.17.3H    CACCATATCA GTAGACACGT CCAAGAACCA GTTCTCCCTG AAGCTGAGTT  227
DP71       CACCATATCA GTAGACACGT CCAAGAACCA GTTCTCCCTG AAGCTGAGCT  250
Consensus  CACCATATCA GTAGACACGT CCAAGAACCA GTTCTCCCTG AAGCTGAGYT  250
                                   CDR3

4.17.3H    CTGTGACCGC TGCGGACACG GCCGTGTATT ACTGTGCCAG GACGTATAGC  277
DP71       CTGTGACCGC TGCGGACACG GCCGTGTATT ACTGTGC--- GA--------  289
Consensus  CTGTGACCGC TGCGGACACG GCCGTGTATT ACTGTGCCAG GACGTATAGC  300

4.17.3H    AGTTCGTTCT ACTACTACGG TATGGACGTC TGGGGCCAAG GGACCACGGT  327
DP71       ---------- ---------- ----GA---- ---------- -GA-------  293
Consensus  AGTTCGTTCT ACTACTACGG TATGGACGTC TGGGGCCAAG GGACCACGGT  350

4.17.3H    CACCGTCTCC TCAG                                          341
DP71       ---------- ----                                          293
Consensus  CACCGTCTCC TCAG                                          364
```

FIG. 3A

| Clone | C domain mutations | FR mutation | CDR mutation | Change in Cys | Change in glycosylation |
|---|---|---|---|---|---|
| 2.13.2 Heavy | 0 | 3 | 8 | 0 | 0 |
| 2.13.2 Light | 0 | 1 | 4 | 1 (CDR3) | 0 |
| 2.12.2 Heavy | 0 | 2 | 8 | 0 | 0 |
| 2.12.2 Light | 0 | 3 | 5 | 0 | 0 |

FIG. 3B

```
PF2 2.13.2 Heavy chain (DP-47 (3-23)/D6-19/JH6)
                                              +
MEFGLSWLFL VAILKGVQCE VQLLZSGGGL VQPGGSLRLS CTASGFTFSS YAMNWVRQAP GKGLEWVSAI SGSGGTTFYA DSVKGRFTIS RDNSRTTLYL
MEFGLSWLFL VAILKGVQCE VQLLZSGGGL VQPGGSLRLS CAASGFTFSS YAMSWVRQAP GKGLEWVSAI SGSGGTTFYA DSVKGRFTIS RDNSRTTLYL
                                      * *                  *

QMNSLRAEDT AVYYCAK--D LGWSDSYYYY YGMDVWGQGT TVTVSSASTK GPSVFPLAPC SRSTSESTAA LGCLVKDYFP EPVTVSWNSG ALTSGVHTFP
QMNSLRAEDT AVYYCAKGYS SGW--YYYYY YGMDVWGQGI TVTVSSASTK GPSVFPLAPC SRSTSESTAA LGCLVKDYFP EPVTVSWNSG ALTSGVHTFP
           * *  ***                      *

AVLQSSGLYS LSSVVTVPSS NFGTQTYTCN VDHKPSNTKV DKTVERKCCV ECPPCPAPPV AGPSVFLFPP KPKDTLMISR TPEVTCVVVD VSHEDPEVQF
AVLQSSGLYS LSSVVTVPSS NFGTQTYTCN VDHKPSNTKV DKTVERKCCV ECPPCPAPPV AGPSVFLFPP KPKDTLMISR TPEVTCVVVD VSHEDPEVQF

NWYVDGVEVH NAKTKPREEQ FNSTFRVVSV LTVVHQDWLN GKEYKCKVSN KGLPAPIEKT ISKTKGQPRE PQVYTLPPSR EEMTKNQVSL TCLVKGFYPS
NWYVDGVEVH NAKTKPREEQ FNSTFRVVSV LTVVHQDWLN GKEYKCKVSN KGLPAPIEKT ISKTKGQPRE PQVYTLPPSR EEMTKNQVSL TCLVKGFYPS
                                                                                                       ++

DIAVEWESNG QPENNYKTTP PMLDSDGSFF LYSKLTVDKS RWQQGNVFSC SVMHEALHNH YTQKSLSLSP GK
DIAVEWESNG QPENNYKTTP PMLDSDGSFF LYSKLTVDKS RWQQGNVFSC SVMHEALHNH YTQKSLSLSP GK
```

```
                                                                                              *   *
MDMRVPAQLL GLLLLWFPGA RCDIQMTQFP SSLSASVGDR VTITCRASQG IRNDLGWYQQ KPGKAPKRLI YAASRLHRGV PSRFSGSGSG TEFTLTISSL
DMRVPAQLLL GLLLLWFPGA RCDIQMTQSP SSLSASVGDR VTITCRASQG IRNDLGWYQQ KPGKAPKRLI YAASSLQSGV PSRFSGSGSG TEFTLTISSL
                  **
QPEDFATYYC LQHNSYPCSF GQGTKLEIKR TVAAPSVFIF PPSDEQLKSG TASVVCLLNN FYPREAKVQW KVDNALQSGN SQESVTEQDS KDSTYSLSST
QPEDFATYYC LQHNSYPYTF GQGTKLEIKR TVAAPSVFIF PPSDEQLKSG TASVVCLLNN FYPREAKVQW KVDNALQSGN SQESVTEQDS KDSTYSLSST

LTLSKADYEK HKVYACEVTH QGLSSPVTKS FNRGEC
LTLSKADYEK HKVYACEVTH QGLSSPVTKS FNRGEC
```

FIG. 3D

PF2 2.12.1 Heavy chain (DP-35--(3-11)/D3-3/JH6)

```
                                                                                                      **
MEFGLSWVFL VAIIKGVQCQ AQLVESGGGL VKPGGSLRLS CAASGFTFSD YYMSWIRQAP GKGLEWVSYI SSSGSTRDYA DSVKGRFTIS RDNAKNSLYL
MEFGLSWVFL VAIIKGVQCQ VQLVESGGGL VKPGGSLRLS CAASGFTFSD YYMSWIRQAP GKGLEWVSYI SSSGSTIYYA DSVKGRFTIS RDNAKNSLYL
              *  * ***
QMNSLRAEDT AVYYCVR--D GVETTF-YYY GVETTFYYYY YYGMDVWGQG TTVTVSSAST KGPSVFPLAP CSRSTSESTA ALGCLVKDYF PEPVTVSWNS GALTSGVHTF
QMNSLRAEDT AVYYCARVLR GVETTFYYYY     YYGMDVWGQG TTVTVSSAST KGPSVFPLAP CSRSTSESTA ALOCLVKDYF PEPVTVSWNS CALTSGVHTF
             +

PAVLQSSGLY SLSSVVTVPS SNFGTQTYTC NVDHKPSNTK VDKTVERKCC VECPPCPAPP VAGPSVFLFP PKPKDTLMIS RTPEVTCVVV DVSHEDPEVQ
PAVLQSSGLY SLSSVVTVPS SNFGTQTYTC NVDHKPSNTK VDKTVERKCC VECPPCPAPP VAGPSVFLFP PKPKDTLMIS RTPEVTCVVV DVSHEDPEVQ

PNWYVDGVEV HNAKTKPREE QFNSTFRVVS VLTVVHQDWL NGKEYKCKVS NKGLPAPIEK TISKTKGQPRE PQVYTLPPS REEMTKNQVS LTCLVKGFYP
PNWYVDGVEV HNAKTKPREE QFNSTFRVVS VLTVVHQDWL NGKEYKCKVS NKGLPAPIEK TISKTKGQPRE PQVYTLPPS REEMTKNQVS LTCLVKGFYP

SDIAVEWESN GQPENNYKTT PPMLDSDGSF FLYSKLTVDK SRWQQGNVFS CSVMHEALHN HYTQKSLSLSP GK
SDIAVEWESN GQPENNYKTT PPMLDSDGSF FLYSKLTVDK SRWQQGNVFS CSVMHEALHN HYTQKSLSLSP GK
```

FIG. 3E

PF2.12.1 Light chain. (A30/JK1)

```
              +              *        *   +
MDMRVPAQLL GLLLLWFPGA RCDIQMTQSP SSLSASVGDR VTFTCRASQD IRRDLGWYQQ KPGKAPKRLI YAASRLQSGV PSRFSGSGSG TEFTLTISSL
MDMRVPAQLL GLLLLWFPGA RCDIQMTQSP SSLSASVGDR VTFTCRASQD IRRDLGWYQQ KPGKAPKRLI YAASRLQSGV PSRFSGSGSG TEFTLTISSL
              +                                                            *
QPEDFATYYC LQHNNYPRTF GQGTEVEIIR TVAAPSVFIF PPSDEQLKSG TASVVCLLNN FYPREAKVQW KVDNALQSGN SQESVTEQDS KDSTYSLSST
QPEDFATYYC LQHNNYPRTF GQGTEVEIIR TVAAPSVFIF PPSDEQLKSG TASVVCLLNN FYPREAKVQW KVDNALQSGN SQESVTEQDS KDSTYSLSST

LTLSKADYEK HKVYACEVTH QGLSSPVTKS FNRGEC
LTLSKADYEK HKVYACEVTH QGLSSPVTKS FNRGEC
```

COMBINATION TREATMENT FOR NON-HEMATOLOGIC MALIGNANCIES

The entire disclosure of parent application 60/588,721 filed Jul. 16, 2004 is fully incorporated herein by reference thereto.

BACKGROUND OF THE INVENTION

The present invention relates to a method of treatment for non-hematologic malignancies comprising the administration of anti-insulin-like growth factor I receptor (IGF-1R) antibodies, in conjunction with other therapeutic agents such as chemotherapeutic agents and hormonal therapy.

The insulin-like growth factor (IGF) signaling system plays an important role in the growth and development of many tissues and regulates overall growth. Insulin-like growth factor (IGF-1) is a 7.5-kD polypeptide that circulates in plasma in high concentrations and is detectable in most tissues. IGF-1 stimulates cell differentiation and cell proliferation, and is required by most mammalian cell types for sustained proliferation. These cell types include, among others, human diploid fibroblasts, epithelial cells, smooth muscle cells, T lymphocytes, neural cells, myeloid cells, chondrocytes, osteoblasts and bone marrow stem cells.

The first step in the transduction pathway leading to IGF-1-stimulated cellular proliferation or differentiation is binding of IGF-1 or IGF-2 (or insulin at supraphysiological concentrations) to the IGF-1 receptor. The IGF-1 receptor (IGF-1R) is composed of two types of subunits: an alpha subunit (a 130-135 kD protein that is entirely extracellular and functions in ligand binding) and a beta subunit (a 95-kD transmembrane protein, with transmembrane and cytoplasmic domains). IGF binding proteins (IGFBPs) have growth inhibiting effects by, at least in part, competitively binding IGFs and preventing their association with IGF-1F. The interactions between IGF-1, IGF-2, IGF1R, and IGFBPs affect many physiological and pathological processes such as development, growth and metabolic regulation.

The IGF-1R is initially synthesized as a single chain pro-receptor polypeptide that is processed by glycosylation, proteolytic cleavage, and covalent bonding to assemble into a mature 460-kD heterotetramer comprising two alpha-subunits and two beta-subunits. The beta subunit(s) possesses ligand-activated tyrosine kinase activity. This activity is implicated in the signaling pathways mediating ligand action which involve autophosphorylation of the beta-subunit and phosphorylation of IGF-1R substrates.

There is considerable evidence for a role for IGF-1 and/or IGF-1R in the maintenance of tumor cells in vitro and in vivo. IGF-1R levels are elevated in tumors of lung (Kaiser et al., *J. Cancer Res. Clin. Oncol.* 119: 665-668, 1993; Moody et al., *Life Sciences* 52: 1161-1173, 1993; Macauley et al., *Cancer Res.*, 50: 2511-2517, 1990), breast (Pollack et al., *Cancer Lett.* 38: 223-230, 1987; Foekens et al., *Cancer Res.* 49: 7002-7009, 1989; Cullen et al., *Cancer Res.* 49: 7002-7009, 1990; Arteaga et al., *J. Clin. Invest.* 84: 1418-1423, 1989), prostate and colon (Remaole-Bennet et al., *J. Clin. Endocrinol. Metab.* 75: 609-616, 1992; Guo et al., *Gastroenterol.* 102: 1101-1108, 1992). In addition, IGF-1 appears to be an autocrine stimulator of human gliomas (Sandberg-Nordqvist et al., *Cancer Res.* 53: 2475-2478, 1993), while IGF-1 stimulated the growth of fibrosarcomas that overexpressed IGF-1R (Butler et al., *Cancer Res.* 58: 3021-27, 1998). In addition, individuals with "high normal" levels of IGF-1 have an increased risk of common cancers compared to individuals with IGF-1 levels in the "low normal" range (Rosen et al., *Trends Endocrinol. Metab.* 10: 136-41, 1999). For a review of the role IGF-1/IGF-1 receptor interaction plays in the growth of a variety of human tumors, see Macaulay, *Br. J. Cancer,* 65: 311-320, 1992.

Numerous classes of antineoplastic agents are currently in use. Docetaxel, one of a group of drugs called "taxanes," which are derived from the bark and needles of yew trees, is the first anticancer agent to show a significantly higher response rate than doxorubicin, a very active agent and widely used chemotherapy in the first-line treatment of metastatic breast cancer. Docetaxel also is the first chemotherapy drug as a single agent to demonstrate increased survival among patients with advanced breast cancer compared to the combination of mitomycin C and vinblastine, a commonly used regimen in this patient population. Median time to progression and time to treatment failure were significantly longer for docetaxel than for mitomycin C in combination with vinblastine, and the one-year survival rate significantly greater. Promising results have also been recorded for docetaxel in other human malignancies, such as ovarian, lung, head and neck, gastric and pancreatic cancers.

Paclitaxel, also a taxane, binds to microtubules and prevents their molecular disassembly, thereby inhibiting mitosis (cell division). With the spindle still in place the cell cannot divide into daughter cells. Paclitaxel is most effective against ovarian carcinomas and advanced breast carcinomas.

Hormonal therapy can be very effective in lowering the risk of recurrence for women with hormone-receptor-positive breast cancer. Tamoxifen is the hormonal therapy that has been around the longest—nearly 30 years. It blocks the effect of estrogen on breast cancer cells, keeping the cells from growing. Tamoxifen can reduce recurrence by 40-50% in post-menopausal women, and by 30-50% in pre-menopausal women. It also lowers the risk of a new breast cancer developing in the unaffected breast, and can slow down the progression of advanced disease.

In recent years, aromatase inhibitors have been used as hormonal therapy. This type of therapy is recommended only for postmenopausal women with hormone-receptor-positive breast cancer. It works by blocking the production of estrogen in muscle and fat tissue, which is the main source of estrogen in women beyond menopause, after which the ovaries stop making significant levels of estrogen.

Prostate cancer is the most common cancer and the second cause of cancer death in men in the United States. About 10% of the initial cases of prostate cancer present with metastatic disease. However, in the rest, metastases will develop despite treatment with surgery, radiation or medical therapy, and those metastases will eventually become refractory to hormonal treatment. The use of chemotherapy in hormone refractory (androgen independent) progressive prostate cancer (HRPC) has been characterized historically by poor efficacy and high toxicity. Newer regimens containing docetaxel have shown a survival benefit over previous palliative regimens. Despite this positive trend, the median survival of HRPC patients treated with docetaxel and prednisone is only 18.9 months; clearly, more effective regimens are required for the treatment of HRPC patients.

Although some currently available anti-cancer treatments have been successful, complete responses to these treatments are infrequently observed, and the patient population refractory to these treatments is still large. Thus, development of new therapeutic regimens, particularly those capable of augmenting or potentiating the anti-tumor activity of other antineoplastic agents, is necessary.

In view of the roles that IGF-1 and IGF-1R have in such disorders as cancer and other proliferative disorders when IGF-1 and/or IGF-1R are overexpressed, antibodies to IGF-1R have been produced that block binding of IGF-1 or IGF-2 to IGF-1R. Such antibodies are described, for example, in International Patent Application No. WO 02/053596, published Jul. 11, 2002; International Patent Application Nos. WO 05/016967 and WO 05/016970, both published Feb. 24, 2005; International Patent Application No. WO 03/106621, published Dec. 24, 2003; International Patent Application No. WO 04/083248, published Sep. 30, 2004; International Patent Application No. WO 03/100008, published Dec. 4, 2003; International Patent Publication WO 04/087756, published Oct. 14, 2004; and International Patent Application No WO 05/005635, published Jan. 26, 2005. Because of their ability to block a tumor cell survival pathway, it is desirable to use such anti-IGF-1R antibodies to treat cancer, particularly non-hematological malignancies, in patients to obtain an improved clinical benefit relative to standard cancer treatment regimes alone.

SUMMARY OF THE INVENTION

The present invention is directed to a method for the treatment of an advanced non-hematologic malignancy in a patient in need of such treatment comprising the step of administering to the patient a therapeutically effective amount of an anti-IGF-1R antibody.

More particularly, the present invention is directed to a method comprising the step of administering to the patient an antibody that specifically binds to IGF-1R in combination with a therapeutically effective amount of at least one agent selected from the group consisting of an alkylating agent, a folate antagonist, a pyrimidine antagonist, a cytotoxic antibiotic, a platinum compound, a taxane, a vinca alkaloid, a topoisomerase inhibitor, an EGFR inhibitor, and a hormonal therapy agent. Preferably the antibody is one that specifically binds to human IGF-1R.

In a preferred embodiment of the present invention, the anti-IGF-1R antibody has the following properties: (a) a binding affinity for human IGF-1R of $K_d$ of $8 \times 10^{-9}$ or less, and (b) inhibition of binding between human IGF-1R and IGF-1 with an $IC_{50}$ of less than 100 nM.

In another preferred embodiment of the present invention, the anti-IGF-1R antibody comprises (a) a heavy chain comprising the amino acid sequences of CDR-1, CDR-2, and CDR-3 of an antibody selected from the group consisting of 2.12.1, 2.13.2, 2.14.3, 4.9.2, 4.17.3, and 6.1.1, and (b) a light chain comprising the amino acid sequences of CDR-1, CDR-2, and CDR-3 of an antibody selected from the group consisting of 2.12.1, 2.13.2, 2.14.3, 4.9.2, 4.17.3, and 6.1.1, or (c) sequences having changes from the CDR sequences of an antibody selected from the group consisting of 2.12.1, 2.13.2, 2.14.3, 4.9.2, 4.17.3, and 6.1.1, said sequences being selected from the group consisting of conservative changes, wherein the conservative changes are selected from the group consisting of replacement of nonpolar residues by other nonpolar residues, replacement of polar charged residues by other polar uncharged residues, replacement of polar charged residues by other polar charged residues, and substitution of structurally similar residues; and non-conservative substitutions, wherein the non-conservative substitutions are selected from the group consisting of substitution of polar charged residue for polar uncharged residues and substitution of nonpolar residues for polar residues, additions and deletions.

The present invention is also directed to a pharmaceutical composition for the treatment of a non-hematologic malignancy comprising (a) a therapeutically effective amount of an antibody that specifically binds IGF-1R, (b) a therapeutically effective amount of at least one agent selected from the group consisting of an alkylating agent, a folate antagonist, a pyrimidine antagonist, a cytotoxic antibiotic, a platinum compound, a taxane, a vinca alkaloid, a topoisomerase inhibitor, an EGFR inhibitor, and a hormonal therapy agent; and (c) a pharmaceutically acceptable carrier.

DETAILED DESCRIPTION OF THE DRAWINGS

FIGS. 1A-1C show alignments of the nucleotide sequences of the light chain variable regions from six human anti-IGF-1R antibodies to each other and to germline sequences. FIG. 1A shows the alignment of the nucleotide sequences of the variable region of the light chain (VL) of antibodies 2.12.1 (SEQ ID NO: 1) 2.13.2 (SEQ ID NO: 5), 2.14.3 (SEQ ID NO: 9) and 4.9.2 (SEQ ID NO: 13) to each other and to the germline Vκ A30 sequence (SEQ ID NO: 39). FIG. 1B shows the alignment of the nucleotide sequence of VL of antibody 4.17.3 (SEQ ID NO: 17) to the germline Vκ O12 sequence (SEQ ID NO: 41). FIG. 1C shows the alignment of the nucleotide sequence of VL of antibody 6.1.1 (SEQ ID NO: 21) to the germline Vκ A27 sequence (SEQ ID NO: 37). The alignments also show the CDR regions of the VL from each antibody. The consensus sequences for FIGS. 1A-1C are shown in SEQ ID NOS: 53-55, respectively.

FIGS. 2A-2D show alignments of the nucleotide sequences of the heavy chain variable regions from six human anti-IGF-1R antibodies to each other and to germline sequences. FIG. 2A shows the alignment of the nucleotide sequence of the VH of antibody 2.12.1 (SEQ ID NO: 3) to the germline VH DP-35 sequence (SEQ ID NO: 29). FIG. 2B shows the alignment of the nucleotide sequence of the VH of antibody 2.14.3 (SEQ ID NO: 11) to the germline VIV-4/4.35 sequence (SEQ ID NO: 43). FIGS. 2C-1 and 2C-2 show the alignments of the nucleotide sequences of the VH of antibodies 2.13.2 (SEQ ID NO: 7), 4.9.2 (SEQ ID NO: 15) and 6.1.1 (SEQ ID NO: 23) to each other and to the germline VH DP-47 sequence (SEQ ID NO: 31). FIG. 2D shows the alignment of the nucleotide sequence of the VH of antibody 4.17.3 (SEQ ID NO: 19) to the germline VH DP-71 sequence (SEQ ID NO: 35). The alignment also shows the CDR regions of the antibodies. The consensus sequences for FIGS. 2A-2D are shown in SEQ ID NOS: 56-59, respectively.

FIG. 3A shows the number of mutations in different regions of the heavy and light chains of 2.13.2 and 2.12.1 compared to the germline sequences. FIGS. 3A-D show alignments of the amino acid sequences from the heavy and light chains of antibodies 2.13.2 and 2.12.1 with the germline sequences from which they are derived. FIG. 3B shows an alignment of the amino acid sequence of the heavy chain of antibody 2.13.2 (SEQ ID NO: 45) with that of germline sequence DP-47(3-23)/D6-19/JH6 (SEQ ID NO: 46). FIG. 3C shows an alignment of the amino acid sequence of the light chain of antibody 2.13.2 (SEQ ID NO: 47) with that of germline sequence A30/Jk2 (SEQ ID NO: 48). FIG. 3D shows an alignment of the amino acid sequence of the heavy chain of antibody 2.12.1 (SEQ ID NO: 49) with that of germline sequence DP-35(3-11)/D3-31JH6 (SEQ ID NO: 50). FIG. 3E shows an alignment of the amino acid sequence of the light chain of antibody 2.12.1 (SEQ ID NO: 51) with that of germline sequence A30/Jk1 (SEQ ID NO: 52). For FIGS. 3B-E, the signal sequences are in italic, the CDRs are underlined, the constant domains are bold, the framework (FR) mutations are highlighted with a plus sign ("+") above the amino acid residue and CDR mutations are highlighted with an asterisk above the amino acid residue.

DETAILED DESCRIPTION OF THE INVENTION

Figure 4:
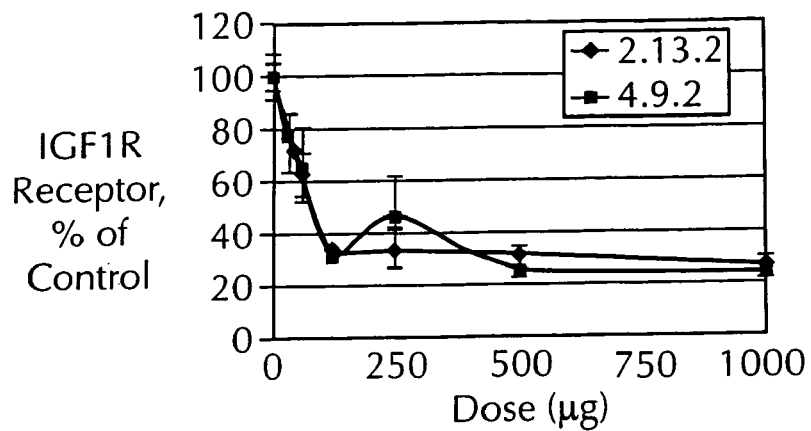
FIG. 4 shows that anti-IGF-1R antibodies 2.13.2 and 4.9.2 reduce IGF-1R phosphotyrosine signal in 3T3-IGF-1R tumors.
Figure 5:
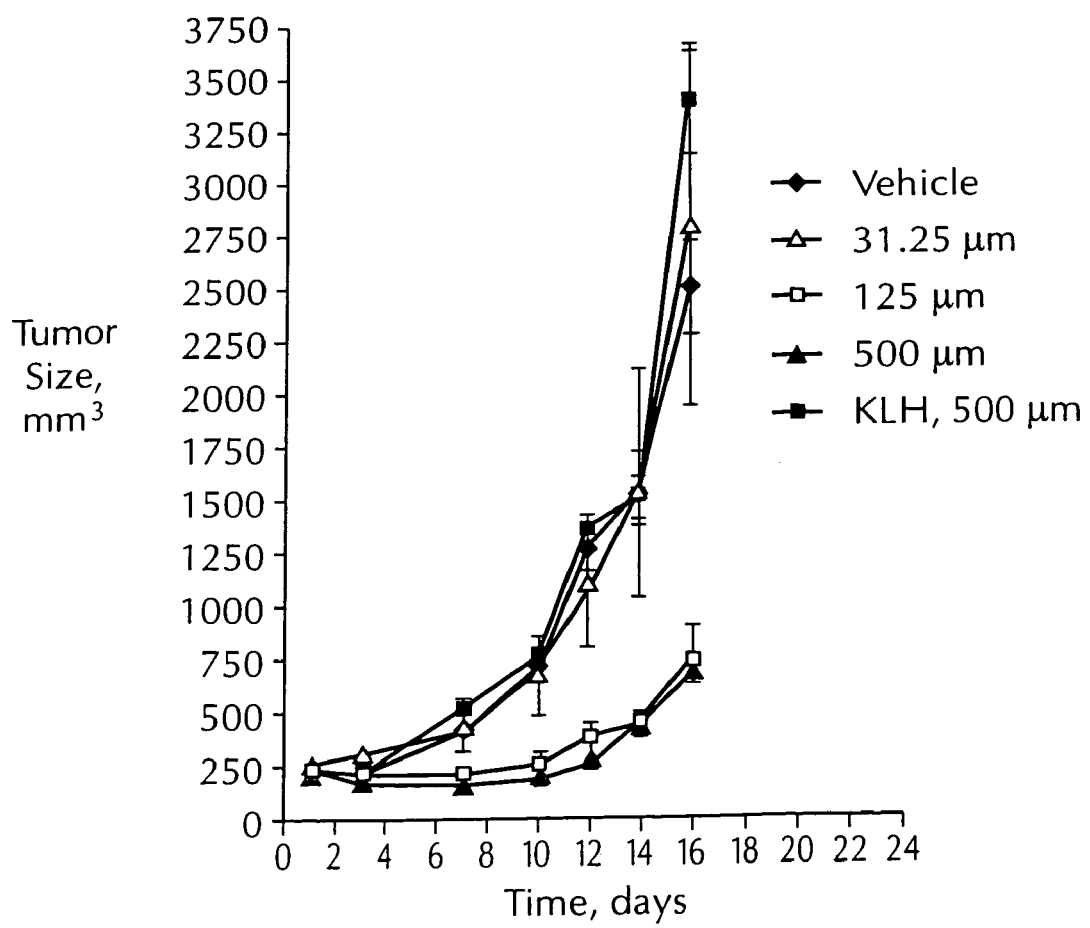
FIG. 5 shows that anti-IGF-1R antibody 2.13.2 inhibits 3T3-IGF-1R tumor growth in vivo.

The present invention are directed to the treatment of non-hematologic malignancies, including breast, lung, brain, skin, ovarian, prostate, head and neck, colorectal, gastric, bladder, renal, esophageal, and pancreatic cancers, as well as solid tumors of childhood. Treatment of both early stage and advanced (metastatic) cancers are within the scope of the present invention. In preferred embodiments, the method of the present invention is used in the treatment of breast cancer, prostate cancer, and non-small cell lung cancer (NSCLC).

There are many classes of chemotherapeutic drugs currently in use for the treatment of non-hematological malignancies that are suitable for use in the combination therapy of the present invention. For example, alkylating agents are a class of drugs that alkylate DNA, restricting uncoiling and replication of strands. Alkylating agents include cyclophosphamide (CYTOXAN), ifosfamide (IFEX), mechlorethamine hydrochloride (MUSTARGEN), thiotepa (THIOPLEX), streptozotocin (ZANOSAR), carmustine (BICNU, GLIADEL WAFER), lomustine (CEENU), and dacarbazine (DTIC-DOME). A preferred alkylating agent for use in the methods of the present invention is cyclophosphamide.

Folate antagonists bind to dihydrofolate reductase (DHFR) and interfere with pyrimidine (thymidine) synthesis. Methotrexate (MATREX, FOLEX, TREXALL), trimetrexate (NEUTREXIN) and pemetrexed (ARIMTA) are folate antagonists suitable for use in the methods of the present invention. In addition to DHFR, pemetrexed also inhibits thymidylate synthase and glycinamide ribonucleotide formyl transferase, two other folate-dependent enzymes involved in thymidine synthesis.

Pyrimidine antagonists inhibit enzymes involved in pyrimidine synthesis. As pyrimidine analogs, they also interfere with DNA production by competing with normal nucleotides for incorporation into the DNA molecule. Pyrimidine antagonists suitable for use in the methods of the present invention include 5-fluorouracil (5-FU); capecitabine (XELODA), a prodrug of 5'-deoxy-5-fluorouridine (5'-FDUR), which is enzymatically converted to 5-FU in vivo; raltitrexed (TOMUDEX); tegafur-uracil (UFTORAL); and gemcitabine (GEMZAR).

Anthracycline antibiotics exert a cytotoxic effect by inhibiting the uncoiling of DNA by intercalation between DNA strands. Anthracyclines and anthracyclines derivatives include doxorubicin hydrochloride (ADRIAMYCIN, RUBEX, DOXIL), epirubicin hydrochloride (ELLENCE, PHARMORUBICIN), daunorubicin (CERUBIDINE, DAUNOXOME), nemorubicin, idarubicin hydrochloride (IDAMYCIN PFS, ZAVEDOS) and mitoxantrone (DHAD, NOVANTRONE). Preferred anthracyclines for use with the present invention include doxorubicin and epirubicin.

Other cytotoxic antibiotics are useful as cancer chemotherapeutic agents and suitable for use in the present invention. These include dactinomycin (actinomycin D, COSMEGEN), plicamycin (MITHRACIN), mitomycin (MUTAMYCIN), and bleomycin (BLENOXANE). Dactinomycin is particularly preferred.

Platinum compounds exert their anti-neoplastic effect by intercalation and intracalation between DNA strands, which inhibits uncoiling of the DNA. Platinum compounds useful in the methods of the present invention include cisplatin (PLATINOL) and carboplatin (PARAPLATIN).

Taxanes promote assembly of microtubules while inhibiting their disassembly into tubulin, thereby blocking a cell's ability to break down the mitotic spindle during mitosis. They have demonstrated significant activity against many solid tumors as single agent therapy and in combination with other chemotherapy agents. One embodiment of the combination therapy of the present invention includes the use of one or more taxanes in combination with the IGF-1R antibody. Suitable taxanes for use in combination with the IGF-1R antibody include docetaxel (TAXOTERE) and paclitaxel (TAXOL).

Vinca alkaloids, like taxanes, are "spindle poisons," acting on the microtubules that form the mitotic spindle. They inhibit mitosis by interfering with microtubule assembly, keeping the spindle from being formed. Vinca alkaloids include vindesine (ELDISINE), vinblastine sulfate (VELBAN), vincristine sulfate (ONCOVIN) and vinorelbine tartrate (NAVELBINE). A preferred vinca alkaloid for use in the methods of the present invention is vinorelbine.

The camptothecin analogs act through inhibition of topoisomerase I, an enzyme critical for DNA replication and packaging. Levels of topoisomerase I are higher in tumor cells than in normal tissue. Camptothecin analogs useful in the methods of the present invention include irinotecan (CAMPTOSAR) and topotecan (HYCAMTIN). Irinotecan is particularly preferred.

Inhibitors of topoisomerase II interfere with the normal DNA breakage resealing process (as do inhibitors of topoisomerase I), and they also interfere with the separation of newly replicated chromosomes, resulting in clastogenic mutation and potential cell death. The anthracyline antibiotics discussed above exhibit topoisomerase II inhibitory activity. Derivatives of podophyllotoxin, an extract of the mayapple that is an antimitotic glucoside) are also topoisomerase II inhibitors. Podophyllotoxin derivatives suitable for use in the present invention include etoposide (VEPESID), etoposide phosphate (ETOPOPHOS), and teniposide (VUMON). Etoposide is particularly preferred.

Compounds directed at inhibition of epidermal growth factor receptor (EGFR) tyrosine kinase (TK) represent a relatively new class of antineoplastic drugs that are useful in the method of the present invention. Many human cancers express members of the EGFR family on the cell surface. When a ligand binds to EGFR, it sets off a cascade of cellular reactions that result in increased cell division and influence other aspects of cancer development and progression, including angiogenesis, metastatic spread, and inhibition of apoptosis. EGFR-TK inhibitors may selectively target one of the members of the EGFR family (EGFR (also known as HER1 or ErbB-1), HER2/neu (also known as ErbB-2), HER3 (also known as ErbB-3), or HER4 (also known as ErbB-4)), or may target two or more of them. EGFR-TK inhibitors suitable for use in the present invention include gefitinib (IRESSA), erlotinib (TARCEVA), trastuzumab (HERCEPTIN), panitumumab (ABX-EGF; Abgenix/Amgen), lapatinib (GlaxoSmithKline), CI-1033 (Pfizer), GW2016 (GlaxoSmithKline), EKB-569 (Wyeth), PKI-166 (Novartis), CP-724,714 (Pfizer), and BIBX-1382 (Boeringer-Ingelheim). Additional EGFR-TK inhibitors are described in United States Patent Publication No. U.S. 2002-0169165A1, published Nov. 14, 2002.

Another embodiment of the combination therapy of the present invention includes the use of hormonal therapy in combination with the IGF-1R antibody, particularly anti-estrogens in the treatment of breast cancer. Some hormonal treatments compete with estrogen for binding sites in breast tissue. These include tamoxifen citrate (NOLVADEX) and fulvestrant (FASLODEX). Similarly, anti-androgens block testosterone receptors and therefore are useful in the treatment of androgen-dependent prostate cancer.

Other hormone treatments include aromatase inhibitors. This class of hormonal agents inactivate aromatase, the enzyme which converts androgens to estrogens. Examples of aromatase inhibitors suitable for use in combination with the IGF-1R antibody include anastrozole (ARIMIDEX), letrozole (FEMARA), exemestane (AROMASIN), and fadrozole hydrochloride. Exemestane is a particularly preferred aromatase inhibitor for use in the methods of the present invention.

Co-administration of the antibody with an additional therapeutic agent (combination therapy) encompasses administering a pharmaceutical composition comprising both the anti-IGF-1 R antibody and one or more additional therapeutic agents, and administering two or more separate pharmaceutical compositions, one comprising the anti-IGF-1R antibody and the other(s) comprising the additional therapeutic agent(s). Further, although co-administration or combination (conjoint) therapy generally mean that the antibody and additional therapeutic agents are administered at the same time as one another, it also encompasses simultaneous, sequential or separate dosing of the individual components of the treatment.

The present invention also encompasses the administration of other therapeutic agents in addition to the first and second components, either concurrently with one or more of those components, or sequentially. Such therapeutic agents include analgesics, cancer vaccines, anti-vascular agents, anti-proliferative agents, and anti-emetic agents. Preferred anti-emetic agents include aprepitant, ondansetron hydrochloride, granisetron hydrochloride, and metoclopramide.

Each administration may vary in its duration from a rapid administration to a continuous perfusion. As a result, for the purposes of the present invention, the combinations are not exclusively limited to those that are obtained by physical association of the constituents, but also to those that permit a separate administration, which can be simultaneous or spaced out over a period of time. The compositions according to the invention are preferably compositions which can be administered parentally. However, these compositions may be administered orally or intraperitoneally in the case of localized regional therapies.

As will be appreciated by one of skill in the art, the choice of therapeutic agents to be used in combination with IGF-1R antibodies, and the timing of their use, will be determined in part by the type and stage of the cancer that is being treated. For example, in early breast cancer (where the cancer has not spread outside the breast), surgery and radiation are generally followed by adjuvant chemotherapy or adjuvant hormonal therapy, either of which may be combined with IGF-1R antibodies in the methods of the present invention. Typical adjuvant chemotherapy for early breast cancer includes cyclophosphamide, methotrexate and 5-FU ("CMF"); 5-FU, doxorubicin, and cyclophosphamide ("FAC"); docetaxel, doxorubicin, and cyclophosphamide ("TAC"); doxorubicin and cyclophosphamide ("AC"); doxorubicin and cyclophosphamide followed by paclitaxel ("AC and T"); and 5-FU, epirubicin, and cyclophosphamide ("FEC"). Tamoxifen is a preferred hormonal treatment at this stage.

In locally advanced breast cancer, wherein the cancer has spread only to nearby tissues or lymph nodes, the patient is often given chemotherapy prior to surgery and radiation, which are then followed by adjuvant hormonal therapy. Alternatively, surgery/radiation is followed by adjuvant chemotherapy, then adjuvant hormonal therapy. IGF-1R antibodies may be administered in conjunction with the chemotherapeutic or hormonal therapy agents whether they are used either before or after surgery/radiation. Typical chemotherapy regimes for locally advanced breast cancer include FAC, AC, FEC, and doxorubicin plus docetaxel ("AT").

Metastatic breast cancer has spread to other parts of the body from the breast in which it started. Chemotherapy optionally may be preceded by hormonal therapy. First line hormonal therapy currently includes tamoxifen and anastrozole. First line chemotherapy regimens currently include FAC, TAC, docetaxel plus epirubicin, docetaxel, paclitaxel, capecitabine, vinorelbine, and trastuzumab. Second line chemotherapy treatments include docetaxel, alone or in combination with capecitabine. The methods of the present invention are suitable for use both as first line therapy and second line therapy.

In the United States, the combination of paclitaxel and carboplatin has become accepted as the standard of care for first line treatment of inoperable Stage IIIB (i.e. cancer has spread to structures near the lung, to lymph nodes in the mediastinum, or to lymph nodes on the other side of the chest or in the lower neck) and Stage IV (i.e. cancer has spread to other parts of the body or to another lobe of the lungs) non-small cell lung cancer (NSCLC). But the overall response rate is only approximately 28% for patients with performance status 0-1 in efficacy studies with a predominantly Stage IV population. In Europe, first line treatment for NSCLC is gemcitabine and cisplatin. Other treatment regimens for NSCLC include paclitaxel alone or with cisplatin or gemcitabine; docetaxel alone or with cisplatin or gemcitabine; vinorelbine alone or with gemcitabine; irinotecan alone or with gemcitabine; pemetrexed; and gefitinib.

It is known that signaling through IGF-1R is required for the tumorgenicity of cell lines and has been shown to decrease the cytotoxicity of chemotherapy, and that blocking IGF-1R activity enhances the effectiveness of current therapies and prevents tumor progression in animal models. It was therefore expected that an inhibitor of IGF-1R such as the antibodies of the present invention would reduce tumor cell survival and enhance the efficacy of chemotherapy when given in combination.

When incubated with cells, fully human monoclonal antibodies that are highly specific and potent inhibitors of IGF-1-induced receptor autophosphorylation induced down-regulation of IGF-1R by receptor internalization. The doses that down-regulated IGF-1R in solid tumor ex vivo models (31.25-125 µg) corresponded to antibody concentrations of 8-40 µg/ml at Day 1 and 2-20 µg/ml at Day 9. Intraperitoneal administration of the anti-IGF-1R antibodies to athymic mice bearing tumors of the transfectant IGF-1R over-expressing NIH-3T3 cell line resulted in a dose dependent inhibition of tumor growth. The serum concentration of anti-IGF-1R antibodies that led to 50% growth inhibition was 20 µg/ml at Day 1, and 13 µg/ml at Day 9. Similar anti-tumor studies were extended to human tumor xenograft models. As a single agent, anti-IGF-1R antibodies inhibited the growth of several xenograft models including breast, lung and colorectal carcinomas.

The combination of anti-IGF-1R antibodies with paclitaxel or carboplatin was tested in the H460 and EBC-1 human NSCLC tumor xenograft models. Combination of anti-IGF-1R antibodies with those agents increased their tumor growth inhibition compared to each agent alone.

Unless otherwise defined herein, scientific, technical, and medical terms used in connection with the present invention shall have the meanings that are commonly understood by those of ordinary skill in the art. Generally, nomenclatures used in connection with, and techniques of, cell and tissue culture, molecular biology, immunology, microbiology, genetics and protein and nucleic acid chemistry described herein are those well known and commonly used in the art.

The following terms, unless otherwise indicated, shall be understood to have the following meanings:

An "antibody" refers to an intact immunoglobulin or to an antigen-binding portion thereof that competes with the intact antibody for specific binding. Antigen-binding portions may be produced by recombinant DNA techniques or by enzymatic or chemical cleavage of intact antibodies. Antigen-binding portions include, inter alia, Fab, Fab', F(ab')$_2$, Fv, dAb, and complementarity determining region (CDR) fragments, single-chain antibodies (scFv), chimeric antibodies, diabodies and polypeptides that contain at least a portion of an immunoglobulin that is sufficient to confer specific antigen binding to the polypeptide.

Immunoglobulin chains exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminus to C-terminus, both light and heavy chains comprise the domains FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, Md. (1987 and 1991)), or Chothia & Lesk, *J. Mol. Biol.* 196:901-917 (1987); Chothia et al., *Nature* 342:878-883 (1989).

An "isolated antibody" is an antibody that (1) is not associated with naturally-associated components, including other naturally-associated antibodies, that accompany it in its native state, (2) is free of other proteins from the same species, (3) is expressed by a cell from a different species, or (4) does not occur in nature. Examples of isolated antibodies include an anti-IGF-1R antibody that has been affinity purified using IGF-1R is an isolated antibody, an anti-IGF-1R antibody that has been synthesized by a hybridoma or other cell line in vitro, and a human anti-IGF-1R antibody derived from a transgenic mouse.

The term "chimeric antibody" refers to an antibody that contains one or more regions from one antibody and one or more regions from one or more other antibodies. In a preferred embodiment, one or more of the CDRs are derived from a human anti-IGF-1R antibody. In a more preferred embodiment, all of the CDRs are derived from a human anti-IGF-1R antibody. In another preferred embodiment, the CDRs from more than one human anti-IGF-1R antibodies are mixed and matched in a chimeric antibody. Further, the framework regions may be derived from one of the same anti-IGF-1R antibodies, from one or more different antibodies, such as a human antibody, or from a humanized antibody.

The term "epitope" includes any protein determinant capable of specific binding to an immunoglobulin or T-cell receptor. Epitopic determinants usually consist of chemically active surface groupings of molecules such as amino acids or sugar sides chains and usually have specific three dimensional structural characteristics, as well as specific charge characteristics. An antibody is said to specifically bind an antigen when the dissociation constant is $\leq 1$ µM, preferably $\leq 100$ nM and most preferably $\leq 10$ nM.

As applied to polypeptides, the term "substantial identity" means that two peptide sequences, when optimally aligned, such as by the programs GAP or BESTFIT using default gap weights, share at least 75% or 80% sequence identity, preferably at least 90% or 95% sequence identity, even more preferably at least 98% or 99% sequence identity. Preferably, residue positions that are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson, *Methods Mol. Biol.* 24: 307-31 (1994). Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; and 6) sulfur-containing side chains are cysteine and methionine. Conservative amino acids substitution groups include: valine-leucine-isoleucine, phenylalanine-tyrosine, lysine-arginine, alanine-valine, glutamate-aspartate, and asparagine-glutamine.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various mutations of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence).

The phrase "in combination with" encompasses simultaneous, sequential or separate dosing of the individual components of the treatment. For example, the antibody may be administered once every three days, while the additional therapeutic agent is administered once daily. The antibody may be administered prior to or subsequent to treatment of the disorder with the additional therapeutic agent. Similarly, the anti-IGF-1R antibody may be administered prior to or subsequent to other therapy, such as radiotherapy, chemotherapy, photodynamic therapy, surgery or other immunotherapy.

The terms "concurrently" and "simultaneously" are used interchangeably and mean the compounds of the combination therapy of the present invention are administered (1) simultaneously in time, or (2) at different times during the course of a common treatment schedule. The term "sequentially" as used herein means administration of the a first component, followed by administration of a second component. Anti-IGF-1R antibodies may be the first component or the second component. After administration of one component, the second component can be administered substantially immediately after the first component, or the second component can be administered an effective time period after the first component; the effective time period is the amount of time given for realization of maximum benefit from the administration of the first component.

The term "patient" includes mammals. In a preferred embodiment, the mammal is a human.

The term "treating," as used herein, unless otherwise indicated, means reversing, alleviating, inhibiting the progress of, or preventing the disorder or condition to which such term applies, or one or more symptoms of such disorder or condition. The term "treatment," as used herein, unless otherwise indicated, refers to the act of treating as "treating" is defined immediately above.

Human antibodies avoid certain of the problems associated with antibodies that possess mouse or rat variable and/or constant regions. More preferred are fully human anti-human IGF-1R antibodies. Fully human anti-IGF-1R antibodies are expected to minimize the immunogenic and allergic responses intrinsic to mouse or mouse-derivatized monoclonal antibodies (Mabs) and thus to increase the efficacy and safety of the administered antibodies. The use of fully human antibodies can be expected to provide a substantial advantage in the treatment of chronic and recurring human diseases, such as inflammation and cancer, which may require repeated antibody administrations. In another embodiment, the invention provides an anti-IGF-1R antibody that does not bind complement.

In another aspect of the invention, the anti-IGF-1R antibodies bind to IGF-1R with high affinity. In one embodiment, the anti-IGF-1R antibody binds to IGF-1R with a $K_d$ of $1 \times 10^{-8}$ M or less. In a more preferred embodiment, the antibody binds to IGF-1R with a $K_d$ or $1 \times 10^{-9}$ M or less. In an even more preferred embodiment, the antibody binds to IGF-1R with a $K_d$ or $5 \times 10^{-10}$ M or less. In another preferred embodiment, the antibody binds to IGF-1R with a $K_d$ or $1 \times 10^{-10}$ M or less. In another preferred embodiment, the antibody binds to IGF-1R with substantially the same $K_d$ as an antibody selected from 2.12.1, 2.13.2, 2.14.3, 3.1.1, 4.9.2, 4.17.3 or 6.1.1. In another preferred embodiment, the antibody binds to IGF-1R with substantially the same $K_d$ as an antibody that comprises one or more CDRs from an antibody selected from 2.12.1, 2.13.2, 2.14.3, 3.1.1, 4.9.2, 4.17.3 or 6.1.1.

The invention also employs an anti-IGF-1R antibody that binds the same antigen or epitope as a human anti-IGF-1R antibody. The invention may also employ an anti-IGF-1R antibody that cross-competes with a human anti-IGF-1R antibody. In a preferred embodiment, the human anti-IGF-1R antibody is 2.12.1, 2.13.2, 2.14.3, 3.1.1, 4.9.2, 4.17.3 or 6.1.1. In another preferred embodiment, the human anti-IGF-1R comprises one or more CDRs from an antibody selected from 2.12.1, 2.13.2, 2.14.3, 3.1.1, 4.9.2, 4.17.3 or 6.1.1

The invention can also be practiced using an anti-IGF-1R antibody that comprises variable sequences encoded by a human κ gene. In a preferred embodiment, the variable sequences are encoded by either the Vκ A27, A30 or O12 gene family. In a preferred embodiment, the variable sequences are encoded by a human Vκ A30 gene family. In a more preferred embodiment, the light chain comprises no more than ten amino acid substitutions from the germline Vκ A27, A30 or O12, preferably no more than six amino acid substitutions, and more preferably no more than three amino acid substitutions. In a preferred embodiment, the amino acid substitutions are conservative substitutions.

In a preferred embodiment, the VL of the anti-IGF-1R antibody contains the same amino acid substitutions, relative to the germline amino acid sequence, as any one or more of the VL of antibodies 2.12.1, 2.13.2, 2.14.3, 3.1.1, 4.9.2, 4.17.3 or 6.1.1.

In another preferred embodiment, the light chain comprises an amino acid sequence that is the same as the amino acid sequence of the VL of 2.12.1, 2.13.2, 2.14.3, 3.1.1, 4.9.2, 4.17.3 or 6.1.1. In another highly preferred embodiment, the light chain comprises amino acid sequences that are the same as the CDR regions of the light chain of 2.12.1, 2.13.2, 2.14.3, 3.1.1, 4.9.2, 4.17.3 or 6.1.1. In another preferred embodiment, the light chain comprises an amino acid sequence from at least one CDR region of the light chain of 2.12.1, 2.13.2, 2.14.3, 3.1.1, 4.9.2, 4.17.3 or 6.1.1.

The present invention can also be carried out using an anti-IGF-1R antibody or portion thereof comprising a human heavy chain or a sequence derived from a human heavy chain. In one embodiment, the heavy chain amino acid sequence is derived from a human $V_H$ DP-35, DP-47, DP-70, DP-71 or VIV-4/4.35 gene family. In a preferred embodiment, the heavy chain amino acid sequence is derived from/a human $V_H$ DP-47 gene family. In a more preferred embodiment, the heavy chain comprises no more than eight amino acid changes from germline $V_H$ DP-35, DP-47, DP-70, DP-71 or VIV-4/4.35, more preferably no more than six amino acid changes, and even more preferably no more than three amino acid changes.

In a preferred embodiment, the VH of the anti-IGF-1R antibody contains the same amino acid substitutions, relative to the germline amino acid sequence, as any one or more of the VH of antibodies 2.12.1, 2.13.2, 2.14.3, 3.1.1, 4.9.2, 4.17.3 or 6.1.1. In another embodiment, the amino acid substitutions are made in the same position as those found in any one or more of the VH of antibodies 2.12.1, 2.13.2, 2.14.3, 3.1.1, 4.17.3., 4.9.2 or 6.1.1, but conservative amino acid substitutions are made rather than using the same amino acid.

In another preferred embodiment, the heavy chain comprises an amino acid sequence that is the same as the amino acid sequence of the VH of 2.12.1, 2.13.2, 2.14.3, 3.1.1, 4.9.2, 4.17.3 or 6.1.1. In another highly preferred embodiment, the heavy chain comprises amino acid sequences that are the same as the CDR regions of the heavy chain of 2.12.1, 2.13.2, 2.14.3, 3.1.1, 4.9.2, 4.17.3 or 6.1.1. In another preferred embodiment, the heavy chain comprises an amino acid sequence from at least one CDR region of the heavy chain of 2.12.1, 2.13.2, 2.14.3, 3.1.1, 4.9.2, 4.17.3 or 6.1.1. In another preferred embodiment, the heavy chain comprises amino acid sequences from CDRs from different heavy chains. In a more preferred embodiment, the CDRs from different heavy chains are obtained from 2.12.1, 2.13.2, 2.14.3, 3.1.1, 4.9.2, 4.17.3 or 6.1.1.

In another embodiment, the invention employs an anti-IGF-1R antibody that inhibits the binding of IGF-1 to IGF-1R or the binding of IGF-2 to IGF-1R. In a preferred embodiment, the IGF-1R is human. In another preferred embodiment, the anti-IGF-1R antibody is a human antibody. In another embodiment, the antibody or portion thereof inhibits binding between IGF-1R and IGF-1 with an $IC_{50}$ of no more than 100 nM. In a preferred embodiment, the $IC_{50}$ is no more than 10 nM. In a more preferred embodiment, the $IC_{50}$ is no more than 5 nM. The $IC_{50}$ can be measured by any method known in the art. Typically, an $IC_{50}$ can be measured by ELISA or RIA. In a preferred embodiment, the $IC_{50}$ is measured by RIA.

In another embodiment, the invention employs an anti-IGF-1R antibody that prevents activation of the IGF-1R in the presence of IGF-i. In another aspect of the invention, the antibody causes the downregulation of IGF-1R from a cell treated with the antibody. In a preferred embodiment, the antibody is selected 2.12.1, 2.13.2, 2.14.3, 3.1.1, 4.9.2, or 6.1.1, or comprises a heavy chain, light chain or antigen-binding region thereof.

Human antibodies can be produced by immunizing a non-human animal comprising of some or all of the human immunoglobulin locus with an IGF-1R antigen. In a preferred embodiment, the non-human animal is a XENOMOUSE™, which is an engineered mouse strain that comprises large fragments of the human immunoglobulin loci and is deficient in mouse antibody production. See, e.g., Green et al. *Nature Genetics* 7:13-21 (1994) and U.S. Pat. Nos. 5,916,771, 5,939, 598, 5,985,615, 5,998,209, 6,075,181, 6,091,001, 6,114,598, and 6,130,364. See also International Patent Application Nos. WO 91/10741, published Jul. 25, 1991; WO 94/02602, published Feb. 3, 1994; WO 96/34096 and WO 96/33735, both published Oct. 31, 1996; WO 98/16654, published Apr. 23, 1998; WO 98/24893, published Jun. 11, 1998; WO 98/50433, published Nov. 12, 1998; WO 99/45031, published Sep. 10, 1999; WO 99/53049, published Oct. 21, 1999; WO 00/09560, published Feb. 24, 2000; and WO 00/037504, published Jun. 29, 2000. The XENOMOUSE™ produces an adult-like human repertoire of fully human antibodies, and generates antigen-specific human monoclonal antibodies. A second generation XENOMOUSE™ contains approximately 80% of the human antibody repertoire through introduction of megabase sized, germline configuration YAC fragments of the human heavy chain loci and κ light chain loci. See Mendez et al. *Nature Genetics* 15:146-156 (1997), Green and Jakobovits *J. Exp. Med.* 188:483-495 (1998).

The IGF-1R antigen can be administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system.

The nucleic acid molecule encoding the variable region of the light chain may be derived from the A30, A27 or O12 Vκ gene. In a preferred embodiment, the light chain is derived from the A30 Vκ gene. In an even more preferred embodiment, the nucleic acid molecule encoding the light chain contains no more than ten amino acid changes from the germline A30 Vκ gene, preferably no more than six amino acid changes, and even more preferably no more than three amino acid changes.

In one embodiment, the antibody contains no greater than ten amino acid changes in either the VH or VL regions of the mutated anti-IGF-1R antibody compared to the anti-IGF-1R antibody prior to mutation. In a more preferred embodiment, there are no more than five amino acid changes in either the VH or VL regions of the mutated anti-IGF-1R antibody, more preferably no more than three amino acid changes. In another embodiment, there are no more than fifteen amino acid changes in the constant domains, more preferably, no more than ten amino acid changes, even more preferably, no more than five amino acid changes.

SEQ ID NOS: 2, 6, 10, 14, 18 and 22 provide the amino acid sequences of the variable regions of six anti-IGF-1R κ light chains. SEQ ID NOS: 4, 8, 12, 16, 20 and 24 provide the amino acid sequences of the variable regions of six anti-IGF-1R heavy chains. SEQ ID NO: 26 depicts the amino acid sequence and SEQ ID NO: 25 depicts the nucleic acid sequence encoding the constant region of the light chain of the anti-IGF-1R antibodies 2.12.1, 2.13.2, 2.14.3, 3.1.1, 4.9.2, 4.17.3 and 6.1.1. SEQ ID NO: 28 depicts the amino acid sequence and SEQ ID NO: 27 depicts the nucleic acid sequence encoding the constant region of the heavy chain of the anti-IGF-1R antibodies 2.12.1, 2.13.2, 2.14.3, 3.1.1, 4.9.2, 4.17.3 and 6.1.1. SEQ ID NOS: 30, 32, 34, 36 and 44 provide the amino acid sequences of the germline heavy chains DP-35, DP-47, DP-70, DP-71 and VIV-4, respectively. SEQ ID NO: 33 provides the nucleotide sequence of the germline heavy chain DP-70. SEQ ID NOS: 38, 40 and 42 provide the amino acid sequences of the three germline κ light chains from which the six anti-IGF-1R κ light chains are derived.

The anti-IGF-1R antibodies can be incorporated into pharmaceutical compositions suitable for administration to a subject. Typically, the pharmaceutical composition comprises an antibody and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Minor amounts of auxiliary substances such as wetting or emulsifying agents, preservatives or buffers, which enhance the shelf life or effectiveness of the antibody or antibody portion, may also be included.

The pharmaceutical compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. A preferred mode of administration is parenteral (e.g., intravenous, subcutaneous, intraperitoneal, intramuscular, or infusion). In a preferred embodiment, the antibody is administered by intravenous infusion or injection. In another preferred embodiment, the antibody is administered by intramuscular or subcutaneous injection. As will be appreciated by the skilled artisan, the route and/or mode of administration will vary depending upon the desired results.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the anti-IGF-1R antibody in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

The pharmaceutical composition may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response. For example, a single bolus may be administered, several divided doses may be administered over time or the dose may be proportionally reduced or increased as indicated by the exigencies of the therapeutic situation. Pharmaceutical composition comprising the antibody or comprising a combination therapy comprising the antibody and one or more additional therapeutic agents may be formulated for single or multiple doses. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals. A particularly useful formulation is 5 mg/ml anti-IGF-1R antibody in a buffer of 20 mM sodium citrate, pH 5.5, 140 mM NaCl, and 0.2 mg/ml polysorbate 80.

The antibody, with or without an additional agent, may be administered once, or more than once for at least the period of time until the condition is treated, palliated or cured. The antibody generally will be administered for as long as the tumor is present provided that the antibody causes the tumor or cancer to stop growing or to decrease in weight or volume. The antibody will generally be administered as part of a pharmaceutical composition as described supra. The dosage of antibody will generally be in the range of 0.025-100 mg/kg, more preferably 0.05-50 mg/kg, more preferably 0.05-20 mg/kg, and even more preferably 0.1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The antibody may be administered from three times daily to once every six months. The administration may be on a schedule such as three times daily, twice daily, once daily, once every two days, once every three days, once weekly, once every two weeks, once every month, once every two months, once every three months and once every six months. The antibody may be administered via an oral, mucosal, buccal, intranasal, inhalable, intravenous, subcutaneous, intramuscular, parenteral, intratumor or topical route.

The antibody may be administered at a site distant from the site of the tumor. The antibody may also be administered continuously via a minipump.

In certain embodiments, the antibody may be administered in an aerosol or inhalable form. Dry aerosol in the form of finely divided solid particles that are not dissolved or suspended in a liquid are also useful in the practice of the present invention. The pharmaceutical formulations of the present invention may be administered in the form of an aerosol spray using for example, a nebulizer such as those described in U.S. Pat. Nos. 4,624,251; 3,703,173; 3,561,444; and 4,635,627.

The serum concentration of the antibody may be measured by any method known in the art. The antibody may also be administered prophylactically in order to prevent a cancer or tumor from occurring. This may be especially useful in patients that have a "high normal" level of IGF-1 because these patients have been shown to have a higher risk of developing common cancers. See Rosen et al., supra.

The antibody employed in the method of the invention can be labeled. This can be done by incorporation of a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

The antibodies employed in the present invention are preferably derived from cells that express human immunoglobulin genes. Use of transgenic mice is known in the art to produce such "human" antibodies. One such method is described in U.S. patent application Ser. No. 08/759,620, filed Dec. 3, 1996. See also Mendez et al. *Nature Genetics*

15:146-156 (1997); Green and Jakobovits *J. Exp. Med.* 188: 483-495 (1998); European Patent No. EP 0 463 151 (grant published Jun. 12, 1996); and International Patent Application Nos. WO 94/02602, published Feb. 3, 1994; WO 96/34096, published Oct. 31, 1996; and WO 98/24893, published Jun. 11, 1998.

As noted above, the invention encompasses use of antibody fragments. Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

In one approach, consensus sequences encoding the heavy and light chain J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors for use in obtaining the antibodies employed in the invention include plasmids, retroviruses, cosmids, YACs, EBV derived episomes, and the like. A convenient vector is normally one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter (Okayama et al. *Mol. Cell. Bio.* 3:280 (1983)), Rous sarcoma virus LTR (Gorman et al. *Proc. Natl. Acad. Sci.* 79:6777 (1982)), and moloney murine leukemia virus LTR (Grosschedl et al. *Cell* 41:885 (1985)); native Ig promoters, etc.

Antibodies that are generated for use in the invention need not initially possess a particular desired isotype. Rather, the antibody as generated can possess any isotype and can be isotype switched thereafter using conventional techniques. These include direct recombinant techniques (see e.g., U.S. Pat. No. 4,816,397), and cell-cell fusion techniques (see e.g., U.S. Pat. No. 5,916,771).

As noted above, the effector function of the antibodies of the invention may be changed by isotype switching to an IgG1, IgG2, IgG3, IgG4, IgD, IgA, IgE, or IgM for various therapeutic uses. Furthermore, dependence on complement for cell killing can be avoided through the use of bispecifics, immunotoxins, or radiolabels, for example.

Bispecific antibodies can be generated that comprise (i) two antibodies: one with a specificity for IGF-1R and the other for a second molecule (ii) a single antibody that has one chain specific for IGF-1R and a second chain specific for a second molecule, or (iii) a single chain antibody that has specificity for IGF-1R and the other molecule. Such bispecific antibodies can be generated using well known techniques, e.g., Fanger et al. *Immunol. Methods* 4:72-81 (1994); Wright and Harris, supra; and Traunecker et al. *Int. J. Cancer* (Suppl.) 7:51-52 (1992).

Antibodies for use in the invention also include "kappabodies" (III et al. *Protein Eng.* 10:949-57 (1997)), "minibodies" (Martin et al. *EMBO J.* 13:5303-9 (1994)), "diabodies" (Holliger et al. *Proc. Natl. Acad. Sci.* (USA) 90:6444-6448 (1993)), and "janusins" (Traunecker et al. *EMBO J.* 10:3655-3659 (1991) and Traunecker et al. *Int. J. Cancer Suppl.* 7:51-52 (1992)) may also be prepared.

The antibodies employed can be modified to act as immunotoxins by conventional techniques. See e.g., Vitetta *Immunol. Today* 14:252 (1993). See also U.S. Pat. No. 5,194,594. Radiolabeled antibodies can also be prepared using well-known techniques. See e.g., Junghans et al. in *Cancer Chemotherapy and Biotherapy* 655-686 (2d edition, Chafner and Longo, eds., Lippincott Raven (1996)). See also U.S. Pat. Nos. 4,681,581, 4,735,210, 5,101,827, 5,102,990 (Re. 35,500), 5,648,471, and 5,697,902.

Particular antibodies useful in practice of the invention include those described in International Patent Application No. WO 02/053596, which further describes antibodies 2.12.1, 2.13.2., 2.14.3, 3.1.1, 4.9.2, and 4.17.3. As disclosed in that published application, hybridomas producing these antibodies were deposited in the American Type Culture Collection (ATCC), 10801 University Boulevard, Manassas, Va. 20110-2209, on Dec. 12, 2000 with the following deposit numbers:

| Hybridoma | Deposit No. |
|---|---|
| 2.12.1 | PTA-2792 |
| 2.13.2 | PTA-2788 |
| 2.14.3 | PTA-2790 |
| 3.1.1 | PTA-2791 |
| 4.9.2 | PTA-2789 |
| 4.17.3 | PTA-2793 |

These antibodies are either fully human IgG2 or IgG4 heavy chains with human kappa light chains. In particular the invention concerns use of antibodies having amino acid sequences of these antibodies.

Antibodies employed in the invention preferably possess very high affinities, typically possessing Kds of from about $10^{-9}$ through about $10^{-11}$ M, when measured by either solid phase or solution phase.

Antibodies used in the present invention can be expressed in cell lines other than hybridoma cell lines. Sequences encoding the cDNAs or genomic clones for the particular antibodies can be used for transformation of suitable mammalian or nonmammalian host cells. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455. Methods for introduction of heterologous polynucleotides into mammalian cells are well known in the art and include, but are not limited to, dextran-mediated transfection, calcium phosphate precipitation, polybrene mediated transfection, protoplast fusion, electroporation, particle bombardment, encapsulation of the polynucleotide(s) in liposomes, peptide conjugates, dendrimers, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, NSO$_0$, HeLa cells, baby hamster kidney (BHK) cells, monkey kidney cells (COS), and human hepatocellular carcinoma cells (e.g., Hep G2). Non-mammalian cells can also be employed, including bacterial, yeast, insect, and plant cells. Site directed mutagenesis of the antibody CH2 domain to eliminate glycosylation may be preferred in order to prevent changes in either the immunogenicity, pharmacokinetic, and/or effector functions resulting from non-human glycosylation. The glutamine synthase system of expression is discussed in whole or part in connection with European Patent Nos. 0 216 846, 0 256 055, and 0 323 997, and European Patent Application No. 89303964.4.

Antibodies for use in the invention can also be produced transgenically through the generation of a mammal or plant that is transgenic for the immunoglobulin heavy and light chain sequences of interest and production of the antibody in a recoverable form therefrom. Transgenic antibodies can be produced in, and recovered from, the milk of goats, cows, or other mammals. See, e.g., U.S. Pat. Nos. 5,827,690, 5,756,687, 5,750,172, and 5,741,957.

The advantages of the present invention can be further appreciated by reference to the following examples. These examples serve intended to illustrate preferred embodiments of the invention and are by no means intended to limit the effective scope of the claims.

EXAMPLE I

Anti-IGF-1R Antibodies in Combination with Docetaxel in the Treatment of Advanced Non-Hematologic Malignancies Patients with advanced-stage non-hematologic malignancies (measurable disease defined by at least one lesion that can be accurately measured and whose size is $\geq 2$ cm×1 cm by conventional computed tomography (CT) scan or $\geq 1$ cm×1 cm by spiral CT scan) received a standard dose of docetaxel (TAXOTERE) (up to 75 mg/m$^2$, using actual body weight to calculate body surface area (BSA)) by intravenous (IV) infusion over 1 hour on Day 1 only of each cycle. After the docetaxel infusion was completed, anti-IGF-1R antibodies as described herein were administered intravenously in a 5 mg/ml liquid formulation at a dose between 0.1 mg/kg and 10 mg/kg. The treatment regimen was repeated after 21 days, with escalation of the anti-IGF-1R antibody dose, and every 21 days thereafter until disease progression or unacceptable toxicity develops for a minimum of 2 cycles and a maximum of 17 cycles. The pre-medication regimen for docetaxel included oral dexamethasone 8 mg twice daily for three days starting one day prior to docetaxel administration. Prophylactic anti-emetics were provided as appropriate.

Dose escalation used an accelerated titration design utilizing a dose-doubling schema with 3-6 subjects per dose level (cohort). Within each new cohort there was no required waiting period between subjects. Subsequent cohorts were not opened until the first subject at the current dose level had been observed for 21 days and subsequent subjects had been observed for 14 days.

The following endpoints were measured: safety, tolerability, pharmacokinetic (PK) parameters of the anti-IGF-1R antibody; human anti-human antibody response (HAHA); response rate and time to progression; and number of circulating tumor cells (CTC) and circulating soluble IGF-1R.

EXAMPLE II

Anti-IGF-1R Antibodies in Combination with Paclitaxel and Carboplatin in the Treatment of Advanced Non-Small Cell Lung Cancer In Part 1 of the study, patients with Stage IIIB or Stage IV or recurrent (after surgery/radiation), measurable, non-small cell lung cancer (NSCLC) who have received no prior chemotherapy received paclitaxel (TAXOL) at a standard dose of 200 mg/m$^2$ by IV infusion over 3 hours. Prior to receiving paclitaxel, all patients received prophylactic anti-allergic/emetic medicines. Carboplatin (PARAPLATIN) was administered by IV infusion over 15-30 minutes; the dose was calculated based on the Calvert formula with a target area under the curve (AUC) of 6 mg/ml×min. After the carboplatin infusion was completed, anti-IGF-1R antibodies as described herein were administered intravenously in a 5 mg/ml formulation at a dose between 0.05 mg/kg and 10 mg/kg. The treatment regimen was repeated after 21 days, with escalation of the anti-IGF-1R antibody dose, and every 21 days thereafter until disease progression or unacceptable toxicity develops, for a minimum of 1 cycle and a maximum of 6 cycles.

Doses were escalated using an accelerated titration design utilizing a dose-doubling schema with 3-6 subjects per cohort. Within each new cohort there was no required waiting period between subjects. Subsequent cohorts were not opened until the first subject at the current dose level has been observed for 21 days and subsequent subjects have been observed for 14 days.

Once at least six patients have been observed for 21 days (i.e., completed one cycle), the randomized second portion of the study will begin.

Part 2 of the study is a two-arm randomized, non-comparative study of anti-IGF-1R antibody in combination with paclitaxel and carboplatin (Arm A) and of paclitaxel and carboplatin alone (Arm B). On Day 1 of Part 2, the patients in both arms are given the same dosages of paclitaxel and carboplatin, over the same time periods, as in the first part. After administration of carboplatin, patients in Arm A are also given the same anti-IGF-1R antibody dose they were given in Part 1. The dose is determined in view of the safety and tolerability demonstrated in Part 1. The treatment is repeated after 21 days, and every 21 days thereafter, until progression or unacceptable toxicity occurs for a minimum of 2 cycles and a maximum of 6.

The following endpoints are measured: PK parameters of the anti-IGF-1R antibody, HAHA, response rate and time to progression, CTC, circulating IGF-1, IGFBPs, and soluble circulating IGF-1R.

EXAMPLE III

Anti-IGF-1R Antibodies in Combination with Docetaxel and Epirubicin in Metastatic Breast Cancer Patients having metastatic breast cancer with at least one lesion that can be accurately measured in two dimensions and whose size is $\geq 2$ cm×1 cm by conventional CT scan or $\geq 1$ cm×1 cm by spiral CT scan are given epirubicin 75 mg/m$^2$ as a single 15 minute infusion. After a one hour pause, docetaxel (TAXOTERE) 75 mg/m$^2$ is administered as a single IV infusion, followed by IV infusion of anti-IGF-1R antibodies as described herein at a dose between 0.05 mg/kg and 10 mg/kg. Prophylactic anti-emetics are given as appropriate. The treatment is repeated after 21 days with escalation of the anti-IGF-1R antibody dose, and every 21 days thereafter until disease progression or unacceptable toxicity develops for a minimum of 2 cycles and a maximum of 6.

Doses are escalated using an accelerated titration design utilizing a dose-doubling schema with 3-6 subjects per cohort. Within each new cohort there is no required waiting period between subjects. Subsequent cohorts may not be opened until the first subject at the current dose level has been observed for 21 days and subsequent subjects have been observed for 14 days.

The following endpoints are measured: PK parameters, HAHA, response rate and time to progression. Time to progression and overall survival are calculated using the Kaplan-Meier product limit method.

EXAMPLE IV

Anti-IGF-1R Antibodies in Combination with Docetaxel and Prednisone in Hormone-Refractory Prostate Cancer Subjects are patients with metastatic adenocarcinoma of the prostate who, after at least one hormonal treatment (orchiectomy, estrogens, LHRH therapy, etc.), have testosterone levels less than 50 ng/dL, prostate-specific antigen (PSA) above 20 ng/mL, and an increase in PSA >50% over nadir value on hormonal therapy measured on 3 successive occasions at least 1 week apart. A pre-medication regimen for docetaxel includes oral dexamethasone 8 mg twice a day given for 3 days starting one day prior to docetaxel administration. A 75 mg/m$^2$ dose of docetaxel (TAXOTERE) (using actual body weight to calculate BSA) is administered by IV infusion over 1 hour on Day 1 only of each cycle. After the docetaxel infusion is completed, anti-IGF-1R antibodies as described herein are administered intravenously in a 5 mg/ml liquid formulation. Prednisone is given daily in two oral 5 mg doses per day, starting on Day 1. Prophylactic anti-emetics may be given as appropriate. The treatment regimen is repeated every 21 days (±3 days) until disease progression or unacceptable toxicity develops, for a maximum of 10 cycles.

The following endpoints are measured: PSA response, population PK parameters of the anti-IGF-1R antibody, HAHA, total number of CTCs and CTCs expressing IGF-1R.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:

1. A method for the treatment of advanced non-small cell lung cancer in a patient in need of such treatment, comprising administering to the patient a therapeutically effective amount of antibody 2.13.2 in combination with a therapeutically effective amount of paclitaxel and a therapeutically effective amount of carboplatin.

2. The method according to claim 1, wherein the antibody is administered at an amount of about 10 mg/kg to about 20 mg/kg.

3. The method according to claim 1, wherein the antibody is administered at an amount between 0.1 mg/kg and 10 mg/kg.

4. The method according to claim 1, wherein the antibody is administered at an amount between 0.05 mg/kg and 20 mg/kg.

5. The method according to claim 1, wherein the antibody is administered every 21 days.

* * * * *

SEQUENCE LISTING

```
<160> NUMBER OF SEQ ID NOS: 60

<210> SEQ ID NO 1
<211> LENGTH: 291
<212> TYPE: DNA
<213> ORGANISM: Homo sapiens

<400> SEQUENCE: 1
tgcatctgta ggagacagag tcaccttcac ttgccgggca agtcaggaca ttagacgtga     60
tttaggctgg tatcagcaga aaccagggaa agctcctaag cgcctgatct atgctgcatc    120
ccgtttacaa agtggggtcc catcaaggtt cagcggcagt ggatctggga cagaattcac    180
tctcacaatc agcagcctgc agcctgaaga ttttgcaact tattactgtc tacagcataa    240
taattatcct cggacgttcg gccaagggac cgaggtggaa atcatacgaa c              291

<210> SEQ ID NO 2
<211> LENGTH: 136
<212> TYPE: PRT
<213> ORGANISM: Homo sapiens

<400> SEQUENCE: 2

Ala Ser Val Gly Asp Arg Val Thr Phe Thr Cys Arg Ala Ser Gln Asp
 1               5                  10                  15

Ile Arg Arg Asp Leu Gly Trp Tyr Gln Gln Lys Pro Gly Lys Ala Pro
            20                  25                  30

Lys Arg Leu Ile Tyr Ala Ala Ser Arg Leu Gln Ser Gly Val Pro Ser
        35                  40                  45

Arg Phe Ser Gly Ser Gly Ser Gly Thr Glu Phe Thr Leu Thr Ile Ser
    50                  55                  60

Ser Leu Gln Pro Glu Asp Phe Ala Thr Tyr Tyr Cys Leu Gln His Asn
65                  70                  75                  80

Asn Tyr Pro Arg Thr Phe Gly Gln Gly Thr Glu Val Glu Ile Ile Arg
                85                  90                  95

Thr Val Ala Ala Pro Ser Val Phe Ile Phe Pro Pro Ser Asp Glu Gln
            100                 105                 110
```

Leu Lys Ser Gly Thr Ala Ser Val Val Cys Leu Leu Asn Asn Phe Tyr
         115                 120                 125

Pro Arg Glu Ala Lys Val Gln Trp
    130                 135

<210> SEQ ID NO 3
<211> LENGTH: 352
<212> TYPE: DNA
<213> ORGANISM: Homo sapiens

<400> SEQUENCE: 3

```
gggaggcttg gtcaagcctg gaggtccctg agactctcct gtgcagcctc tggattcact    60
ttcagtgact actatatgag ctggatccgc caggctccag ggaagggct ggaatgggtt    120 tcatacatta gtagtagtgg tagtaccaga gactacgcac actctgtgaa gggccgattc    180
accatctcca gggacaacgc caagaactca ctgtatctgc aaatgaacag cctgagagcc    240
gaggacacgg ccgtgtatta ctgtgtgaga gatggagtgg aaactacttt ttactactac    300
tactacggta tggacgtctg gggccaaggg accacggtca ccgtctcctc ag           352
```

<210> SEQ ID NO 4
<211> LENGTH: 174
<212> TYPE: PRT
<213> ORGANISM: Homo sapiens

<400> SEQUENCE: 4

Gly Arg Leu Gly Gln Ala Trp Arg Ser Leu Arg Leu Ser Cys Ala Ala
1               5                   10                  15

Ser Gly Phe Thr Phe Ser Asp Tyr Tyr Met Ser Trp Ile Arg Gln Ala
            20                  25                  30

Pro Gly Lys Gly Leu Glu Trp Val Ser Tyr Ile Ser Ser Ser Gly Ser
        35                  40                  45

Thr Arg Asp Tyr Ala Asp Ser Val Lys Gly Arg Phe Thr Ile Ser Arg
    50                  55                  60

Asp Asn Ala Lys Asn Ser Leu Tyr Leu Gln Met Asn Ser Leu Arg Ala
65                  70                  75                  80

Glu Asp Thr Ala Val Tyr Tyr Cys Val Arg Asp Gly Val Glu Thr Thr
                85                  90                  95

Phe Tyr Tyr Tyr Tyr Gly Met Asp Val Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ser Cys Ala
                165                 170

<210> SEQ ID NO 5
<211> LENGTH: 322
<212> TYPE: DNA
<213> ORGANISM: Homo sapiens

<400> SEQUENCE: 5

```
gacatccaga tgacccagtt tccatcctcc ctgtctgcat ctgtaggaga cagagtcacc    60
atcacttgcc gggcaagtca gggcattaga aatgatttag gctggtatca gcagaaacca    120
```

```
gggaaagccc ctaagcgcct gatctatgct gcatcccgtt tgcacagagg ggtcccatca      180
aggttcagcg gcagtggatc tgggacagaa ttcactctca caatcagcag cctgcagcct      240
gaagattttg caacttatta ctgtttacaa cataatagtt acccgtgcag ttttggccag      300
gggaccaagc tggagatcaa ac                                                322
```

<210> SEQ ID NO 6
<211> LENGTH: 107
<212> TYPE: PRT
<213> ORGANISM: Homo sapiens

<400> SEQUENCE: 6

```
Asp Ile Gln Met Thr Gln Phe Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Arg Leu His Arg Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Cys
                85                  90                  95

Ser Phe Gly Gln Gly Thr Lys Leu Glu Ile Lys
            100                 105
```

<210> SEQ ID NO 7
<211> LENGTH: 375
<212> TYPE: DNA
<213> ORGANISM: Homo sapiens

<400> SEQUENCE: 7

```
aggtgcagct gttggagtct gggggaggct tggtacagcc tggggggtcc ctgagactct      60
cctgtacagc ctctggattc acctttagca gctatgccat gaactgggtc cgccaggctc      120
cagggaaggg gctggagtgg gtctcagcta ttagtggtag tggtggtacc acattctacg      180
cagactccgt gaagggccgg ttcaccatct ccagagacaa ttccaggacc acgctgtatc      240
tgcaaatgaa cagcctgaga gccgaggaca cggccgtata ttactgtgcg aaagatcttg      300
gctggtccga ctcttactac tactactacg gtatggacgt ctggggccaa gggaccacgg      360
tcaccgtctc ctcag                                                        375
```

<210> SEQ ID NO 8
<211> LENGTH: 124
<212> TYPE: PRT
<213> ORGANISM: Homo sapiens

<400> SEQUENCE: 8

```
Val Gln Leu Leu Glu Ser Gly Gly Gly Leu Val Gln Pro Gly Gly Ser
1               5                   10                  15

Leu Arg Leu Ser Cys Thr Ala Ser Gly Phe Thr Phe Ser Ser Tyr Ala
            20                  25                  30

Met Asn Trp Val Arg Gln Ala Pro Gly Lys Gly Leu Glu Trp Val Ser
        35                  40                  45

Ala Ile Ser Gly Ser Gly Gly Thr Thr Phe Tyr Ala Asp Ser Val Lys
    50                  55                  60
```

Gly Arg Phe Thr Ile Ser Arg Asp Asn Ser Arg Thr Thr Leu Tyr Leu
65                  70                  75                  80

Gln Met Asn Ser Leu Arg Ala Glu Asp Thr Ala Val Tyr Tyr Cys Ala
                85                  90                  95

Lys Asp Leu Gly Trp Ser Asp Ser Tyr Tyr Tyr Tyr Gly Met Asp
            100                 105                 110

Val Trp Gly Gln Gly Thr Thr Val Thr Val Ser Ser
        115                 120

<210> SEQ ID NO 9
<211> LENGTH: 302
<212> TYPE: DNA
<213> ORGANISM: Homo sapiens

<400> SEQUENCE: 9
tcctccctgt ctgcatctgt aggagacaga gtcaccttca cttgccgggc aagtcaggac      60
attagacgtg atttaggctg gtatcagcag aaaccaggaa agctcctaa gcgcctgatc     120 tatgctgcat cccgtttaca agtggggtc ccatcaaggt tcagcggcag tggatctggg     180
acagaattca ctctcacaat cagcagcctg cagcctgaag attttgcaac ttattactgt     240
ctacagcata taattatcc tcggacgttc ggccaaggga ccgaggtgga aatcatacga     300
ac                                                                    302

<210> SEQ ID NO 10
<211> LENGTH: 100
<212> TYPE: PRT
<213> ORGANISM: Homo sapiens

<400> SEQUENCE: 10

Ser Ser Leu Ser Ala Ser Val Gly Asp Arg Val Thr Phe Thr Cys Arg
1               5                   10                  15

Ala Ser Gln Asp Ile Arg Arg Asp Leu Gly Trp Tyr Gln Gln Lys Pro
                20                  25                  30

Gly Lys Ala Pro Lys Arg Leu Ile Tyr Ala Ala Ser Arg Leu Gln Ser
            35                  40                  45

Gly Val Pro Ser Arg Phe Ser Gly Ser Gly Ser Gly Thr Glu Phe Thr
    50                  55                  60

Leu Thr Ile Ser Ser Leu Gln Pro Glu Asp Phe Ala Thr Tyr Tyr Cys
65                  70                  75                  80

Leu Gln His Asn Asn Tyr Pro Arg Thr Phe Gly Gln Gly Thr Glu Val
                85                  90                  95

Glu Ile Ile Arg
            100

<210> SEQ ID NO 11
<211> LENGTH: 338
<212> TYPE: DNA
<213> ORGANISM: Homo sapiens

<400> SEQUENCE: 11
gggcccagga ctggtgaagc cttcggagac cctgtccctc acctgcactg tctctggtgg     60
ctccatcagt aattactact ggagctggat ccggcagccc gccgggaagg gactggagtg    120
gattgggcgt atctatacca gtgggagccc caactacaac ccctccctca gagtcgagt     180 caccatgtca gtagacacgt ccaagaacca gttctccctg aagctgaact ctgtgaccgc    240
cgcggacacg gccgtgtatt actgtgcggt aacgattttt ggagtggtta ttatctttga    300
ctactggggc agggaaccc tggtcaccgt ctcctcag 338

<210> SEQ ID NO 12
<211> LENGTH: 112
<212> TYPE: PRT
<213> ORGANISM: Homo sapiens

<400> SEQUENCE: 12

Gly Pro Gly Leu Val Lys Pro Ser Glu Thr Leu Ser Leu Thr Cys Thr
1               5                   10                  15

Val Ser Gly Gly Ser Ile Ser Asn Tyr Tyr Trp Ser Trp Ile Arg Gln
            20                  25                  30

Pro Ala Gly Lys Gly Leu Glu Trp Ile Gly Arg Ile Tyr Thr Ser Gly
        35                  40                  45

Ser Pro Asn Tyr Asn Pro Ser Leu Lys Ser Arg Val Thr Met Ser Val
    50                  55                  60

Asp Thr Ser Lys Asn Gln Phe Ser Leu Lys Leu Asn Ser Val Thr Ala
65                  70                  75                  80

Ala Asp Thr Ala Val Tyr Tyr Cys Ala Val Thr Ile Phe Gly Val Val
                85                  90                  95

Ile Ile Phe Asp Tyr Trp Gly Gln Gly Thr Leu Val Thr Val Ser Ser
            100                 105                 110

<210> SEQ ID NO 13
<211> LENGTH: 322
<212> TYPE: DNA
<213> ORGANISM: Homo sapiens

<400> SEQUENCE: 13
gacatccaga tgacccagtc tccatcctcc ctgtctgcat ctgtaggaga cagagtcacc    60
atcacttgcc gggcaagtca gggcattaga agtgatttag ctggtttca gcagaaacca   120 gggaaagccc ctaagcgcct gatctatgct gcatccaaat tacaccgtgg ggtcccatca   180
aggttcagcg gcagtggatc tgggacagaa ttcactctca caatcagccg cctgcagcct   240
gaagattttg caacttatta ctgtctacag cataatagtt accctctcac tttcggcgga   300
gggaccaagg tggagatcaa ac                                            322

<210> SEQ ID NO 14
<211> LENGTH: 107
<212> TYPE: PRT
<213> ORGANISM: Homo sapiens

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Asp
            20                  25                  30

Leu Gly Trp Phe Gln Gln Lys Pro Gly Lys Ala Pro Lys Arg Leu Ile
        35                  40                  45

Tyr Ala Ala Ser Lys Leu His Arg Gly Val Pro Ser Arg Phe Ser Gly
    50                  55                  60

Ser Gly Ser Gly Thr Glu Phe Thr Leu Thr Ile Ser Arg Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys
            100                 105

<210> SEQ ID NO 15
<211> LENGTH: 376
<212> TYPE: DNA
<213> ORGANISM: Homo sapiens

<400> SEQUENCE: 15

```
gaggtgcagc tgttggagtc tgggggaggc ttggtacagc ctgggggtc cctgagactc      60
tcctgtgcag cctctggatt cacctttagc agctatgcca tgagctgggt ccgccaggct    120
ccagggaagg ggctggagtg ggtctcagct attagtggta gtggtggtat cacatactac    180
gcagactccg tgaagggccg gttcaccatc tccagagaca attccaagaa cacgctgtat    240
ctgcaaatga acagcctgag agccgaggac acggccgtat attactgtgc gaaagatctg    300
ggctacggtg acttttacta ctactactac ggtatggacg tctggggcca agggaccacg    360
gtcaccgtct cctcag                                                    376
```

<210> SEQ ID NO 16
<211> LENGTH: 125
<212> TYPE: PRT
<213> ORGANISM: Homo sapiens

<400> SEQUENCE: 16

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Gly Tyr Gly Asp Phe Tyr Tyr Tyr Tyr Gly Met
            100                 105                 110

Asp Val Trp Gly Gln Gly Thr Thr Val Thr Val Ser Ser
        115                 120                 125
```

<210> SEQ ID NO 17
<211> LENGTH: 279
<212> TYPE: DNA
<213> ORGANISM: Homo sapiens

<400> SEQUENCE: 17

```
caggagacag agtcaccatc acttgccggg caagtcagag cattagtacc tttttaaatt      60
ggtatcagca gaaaccaggg aaagccccta aactcctgat ccatgttgca tccagtttac    120
aaggtggggt cccatcaagg ttcagtggca gtggatctgg gacagatttc actctcacca    180
tcagcagtct gcaacctgaa gattttgcaa cttactactg tcaacagagt tacaatgccc    240
cactcacttt cggcggaggg accaaggtgg agatcaaac                           279
```

<210> SEQ ID NO 18
<211> LENGTH: 92
<212> TYPE: PRT
<213> ORGANISM: Homo sapiens

<400> SEQUENCE: 18

Gly Asp Arg Val Thr Ile Thr Cys Arg Ala Ser Gln Ser Ile Ser Thr
1               5                   10                  15

Phe Leu Asn Trp Tyr Gln Gln Lys Pro Gly Lys Ala Pro Lys Leu Leu
            20                  25                  30

Ile His Val Ala Ser Ser Leu Gln Gly Gly Val Pro Ser Arg Phe Ser
        35                  40                  45

Gly Ser Gly Ser Gly Thr Asp Phe Thr Leu Thr Ile Ser Ser Leu Gln
    50                  55                  60

Pro Glu Asp Phe Ala Thr Tyr Tyr Cys Gln Gln Ser Tyr Asn Ala Pro
65                  70                  75                  80

Leu Thr Phe Gly Gly Gly Thr Lys Val Glu Ile Lys
                85                  90

<210> SEQ ID NO 19
<211> LENGTH: 341
<212> TYPE: DNA
<213> ORGANISM: Homo sapiens

<400> SEQUENCE: 19
cccaggactg gtgaagcctt cggagaccct gtccctcacc tgcactgtct ctggtggctc    60
catcagtagt tactactgga gttggatccg gcagccccca gggaagggac tggagtggat   120
tgggtatatc tattacagtg ggagcaccaa ctacaacccc tccctcaaga gtcgagtcac   180
catatcagta gacacgtcca agaaccagtt ctccctgaag ctgagttctg tgaccgctgc   240
ggacacggcc gtgtattact gtgccaggac gtatagcagt tcgttctact actacggtat   300
ggacgtctgg ggccaaggga ccacggtcac cgtctcctca g                      341

<210> SEQ ID NO 20
<211> LENGTH: 113
<212> TYPE: PRT
<213> ORGANISM: Homo sapiens

<400> SEQUENCE: 20

Pro Gly Leu Val Lys Pro Ser Glu Thr Leu Ser Leu Thr Cys Thr Val
1               5                   10                  15

Ser Gly Gly Ser Ile Ser Ser Tyr Tyr Trp Ser Trp Ile Arg Gln Pro
            20                  25                  30

Pro Gly Lys Gly Leu Glu Trp Ile Gly Tyr Ile Tyr Tyr Ser Gly Ser
        35                  40                  45

Thr Asn Tyr Asn Pro Ser Leu Lys Ser Arg Val Thr Ile Ser Val Asp
    50                  55                  60

Thr Ser Lys Asn Gln Phe Ser Leu Lys Leu Ser Ser Val Thr Ala Ala
65                  70                  75                  80

Asp Thr Ala Val Tyr Tyr Cys Ala Arg Thr Tyr Ser Ser Ser Phe Tyr
                85                  90                  95

Tyr Tyr Gly Met Asp Val Trp Gly Gln Gly Thr Thr Val Thr Val Ser
            100                 105                 110

Ser

<210> SEQ ID NO 21
<211> LENGTH: 274
<212> TYPE: PRT
<213> ORGANISM: Homo sapiens

<400> SEQUENCE: 21

```
Ala Gly Ala Gly Cys Cys Ala Cys Cys Thr Cys Thr Cys Thr
 1               5                  10                  15

Gly Thr Ala Gly Gly Cys Cys Ala Gly Thr Cys Ala Gly Ala Gly
            20                  25                  30

Thr Gly Thr Thr Cys Gly Cys Gly Gly Cys Ala Gly Thr Ala Cys
             35                  40                  45

Thr Thr Ala Gly Cys Cys Thr Gly Gly Thr Ala Cys Ala Gly Cys
         50                  55                  60

Ala Gly Ala Ala Ala Cys Cys Thr Gly Cys Cys Ala Gly Gly Cys
 65                  70                  75                  80

Thr Cys Cys Cys Ala Gly Cys Thr Cys Thr Cys Ala Thr Cys
             85                  90                  95

Thr Ala Thr Gly Gly Thr Gly Cys Ala Thr Cys Ala Gly Cys Ala
             100                 105                 110

Gly Gly Gly Cys Cys Ala Cys Thr Gly Cys Ala Thr Cys Cys Cys
         115                 120                 125

Ala Gly Ala Cys Ala Gly Gly Thr Thr Cys Ala Gly Thr Gly Gly Cys
 130                 135                 140

Ala Gly Thr Gly Gly Gly Thr Cys Thr Gly Gly Gly Ala Cys Ala Gly
 145                 150                 155                 160

Ala Cys Thr Thr Cys Ala Cys Thr Cys Thr Cys Ala Cys Cys Ala Thr
             165                 170                 175

Cys Ala Gly Cys Ala Gly Ala Cys Thr Gly Gly Ala Gly Cys Cys Thr
             180                 185                 190

Gly Ala Ala Gly Ala Thr Thr Thr Thr Gly Cys Ala Gly Thr Gly Thr
             195                 200                 205

Thr Thr Thr Ala Cys Thr Gly Thr Cys Ala Gly Cys Ala Gly Thr Ala
             210                 215                 220

Thr Gly Gly Thr Ala Gly Thr Thr Cys Ala Cys Cys Thr Cys Gly Asn
 225                 230                 235                 240

Ala Cys Gly Thr Thr Cys Gly Cys Cys Ala Ala Gly Gly Gly Ala
             245                 250                 255

Cys Cys Ala Ala Gly Gly Thr Gly Ala Ala Ala Thr Cys Ala Ala
             260                 265                 270

Ala Cys

<210> SEQ ID NO 22
<211> LENGTH: 91
<212> TYPE: PRT
<213> ORGANISM: Homo sapiens

<400> SEQUENCE: 22

Arg Ala Thr Leu Ser Cys Arg Ala Ser Gln Ser Val Arg Gly Arg Tyr
 1               5                  10                  15

Leu Ala Trp Tyr Gln Gln Lys Pro Gly Gln Ala Pro Arg Leu Leu Ile
             20                  25                  30

Tyr Gly Ala Ser Ser Arg Ala Thr Gly Ile Pro Asp Arg Phe Ser Gly
         35                  40                  45

Ser Gly Ser Gly Thr Asp Phe Thr Leu Thr Ile Ser Arg Leu Glu Pro
     50                  55                  60

Glu Asp Phe Ala Val Phe Tyr Cys Gln Gln Tyr Gly Ser Ser Pro Arg
 65                  70                  75                  80

Thr Phe Gly Gln Gly Thr Lys Val Glu Ile Lys
             85                  90
```

<210> SEQ ID NO 23
<211> LENGTH: 367
<212> TYPE: DNA
<213> ORGANISM: Homo sapiens

<400> SEQUENCE: 23

```
gaggtgcagc tgttggagtc tgggggaggc ttggtacagc ctgggggtc cctgagactc      60 tcctgtgcag cctctggatt cacctttagc agctatgcca tgagctgggt ccgccaggct     120
ccagggaagg ggctggagtg ggtctcaggt attactggga gtggtggtag tacatactac     180
gcagactccg tgaagggccg gttcaccatc tccagagaca attccaagaa cacgctgtat     240
ctgcaaatga acagcctgag agccgaggac acggccgtat attactgtgc gaaagatcca     300
gggactacgg tgattatgag ttggttcgac ccctggggcc agggaaccct ggtcaccgtc     360
tcctcag                                                               367
```

<210> SEQ ID NO 24
<211> LENGTH: 122
<212> TYPE: PRT
<213> ORGANISM: Homo sapiens

<400> SEQUENCE: 24

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Thr Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Gly Thr Thr Val Ile Met Ser Trp Phe Asp Pro Trp
            100                 105                 110

Gly Gln Gly Thr Leu Val Thr Val Ser Ser
        115                 120
```

<210> SEQ ID NO 25
<211> LENGTH: 320
<212> TYPE: DNA
<213> ORGANISM: Homo sapiens

<400> SEQUENCE: 25

```
gaactgtggc tgcaccatct gtcttcatct tcccgccatc tgatgagcag ttgaaatctg      60
gaactgcctc tgttgtgtgc ctgctgaata acttctatcc cagagaggcc aaagtacagt     120
ggaaggtgga taacgccctc caatcgggta actcccagga gagtgtcaca gagcaggaca     180
gcaaggacag cacctacagc ctcagcagca cgctgacgct gagcaaagca gactacgaga     240
aacacaaagt ctacgcctgc gaagtcaccc atcagggcct gagctcgccc gtcacaaaga     300
gcttcaacag gggagagtgt                                                  320
```

<210> SEQ ID NO 26
<211> LENGTH: 106
<212> TYPE: PRT
<213> ORGANISM: Homo sapiens

<400> SEQUENCE: 26

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 27
<211> LENGTH: 978
<212> TYPE: DNA
<213> ORGANISM: Homo sapiens

<400> SEQUENCE: 27
gcctccacca agggcccatc ggtcttcccc ctggcgccct gctccaggag cacctccgag     60
agcacagcgg ccctgggctg cctggtcaag gactacttcc ccgaaccggt gacggtgtcg    120
tggaactcag gcgctctgac cagcggcgtg cacaccttcc cagctgtcct acagtcctca    180
ggactctact ccctcagcag cgtggtgacc gtgccctcca gcaacttcgg cacccagacc    240
tacacctgca acgtagatca caagcccagc aacaccaagg tggacaagac agttgagcgc    300
aaatgttgtg tcgagtgccc accgtgccca gcaccacctg tggcaggacc gtcagtcttc    360
ctcttccccc caaaacccaa ggacaccctc atgatctccc ggacccctga ggtcacgtgc    420
gtggtggtgg acgtgagcca cgaagacccc gaggtccagt tcaactggta cgtggacggc    480
gtggaggtgc ataatgccaa gacaaagcca cgggaggagc agttcaacag cacgttccgt    540
gtggtcagcg tcctcaccgt tgtgcaccag gactggctga acggcaagga gtacaagtgc    600
aaggtctcca acaaaggcct cccagccccc atcgagaaaa ccatctccaa aaccaaaggg    660
cagccccgag aaccacaggt gtacaccctg cccccatccc gggaggagat gaccaagaac    720
caggtcagcc tgacctgcct ggtcaaaggc ttctaccccg cgacatcgc cgtggagtgg    780
gagagcaatg ggcagccgga gaacaactac aagaccacac ctcccatgct ggactccgac    840
ggctccttct tcctctacag caagctcacc gtggacaaga gcaggtggca gcaggggaac    900
gtcttctcat gctccgtgat gcatgaggct ctgcacaacc actacacgca gaagagcctc    960
tccctgtctc cgggtaaa                                                  978

<210> SEQ ID NO 28
<211> LENGTH: 326
<212> TYPE: PRT
<213> ORGANISM: Homo sapiens

<400> SEQUENCE: 28

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 29
<211> LENGTH: 296
<212> TYPE: DNA
<213> ORGANISM: Homo sapiens

<400> SEQUENCE: 29
caggtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg gctggagtg ggtttcatac attagtagta gtggtagtac catatactac     180
gcagactctg tgaagggccg attcaccatc tccagggaca cgccaagaa ctcactgtat     240 ctgcaaatga acagcctgag agccgaggac acggccgtgt attactgtgc gagaga         296

<210> SEQ ID NO 30
<211> LENGTH: 98

<212> TYPE: PRT
<213> ORGANISM: Homo sapiens

<400> SEQUENCE: 30

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg
```

<210> SEQ ID NO 31
<211> LENGTH: 296
<212> TYPE: PRT
<213> ORGANISM: Homo sapiens

<400> SEQUENCE: 31

```
Gly Ala Gly Gly Thr Gly Cys Ala Gly Cys Thr Gly Thr Thr Gly Gly
1               5                   10                  15

Ala Gly Thr Cys Thr Gly Gly Gly Gly Gly Ala Gly Gly Cys Thr Thr
            20                  25                  30

Gly Gly Thr Ala Cys Ala Gly Cys Cys Thr Gly Gly Gly Gly Gly Gly
        35                  40                  45

Thr Cys Cys Cys Thr Gly Ala Gly Ala Cys Thr Cys Thr Cys Cys Thr
    50                  55                  60

Gly Thr Gly Cys Ala Gly Cys Cys Thr Cys Thr Gly Gly Ala Thr Thr
65                  70                  75                  80

Cys Ala Cys Cys Thr Thr Thr Ala Gly Cys Ala Gly Cys Thr Ala Thr
                85                  90                  95

Gly Cys Cys Ala Thr Gly Ala Gly Cys Thr Gly Gly Gly Thr Cys Cys
            100                 105                 110

Gly Cys Cys Ala Gly Gly Cys Thr Cys Cys Ala Gly Gly Gly Ala Ala
        115                 120                 125

Gly Gly Gly Gly Cys Thr Gly Gly Ala Gly Thr Gly Gly Gly Thr Cys
    130                 135                 140

Thr Cys Ala Gly Cys Thr Ala Thr Thr Ala Gly Thr Gly Gly Thr Ala
145                 150                 155                 160

Gly Thr Gly Gly Thr Gly Gly Thr Ala Gly Cys Ala Cys Ala Thr Ala
                165                 170                 175

Cys Thr Ala Cys Gly Cys Ala Gly Ala Cys Thr Cys Cys Gly Thr Gly
            180                 185                 190

Ala Ala Gly Gly Gly Cys Cys Gly Gly Thr Thr Cys Ala Cys Cys Ala
        195                 200                 205

Thr Cys Thr Cys Cys Ala Gly Ala Gly Ala Cys Ala Ala Thr Thr Cys
    210                 215                 220

Cys Ala Ala Gly Ala Ala Cys Ala Cys Gly Cys Thr Gly Thr Ala Thr
225                 230                 235                 240

Cys Thr Gly Cys Ala Ala Ala Thr Gly Ala Ala Cys Ala Gly Cys Cys
```

```
                    245                 250                 255
Thr Gly Ala Gly Ala Gly Cys Cys Gly Ala Gly Ala Cys Ala Cys
                260                 265                 270

Gly Gly Cys Cys Gly Thr Ala Thr Ala Thr Ala Cys Thr Gly Thr
            275                 280                 285

Gly Cys Gly Ala Ala Ala Gly Ala
        290                 295

<210> SEQ ID NO 32
<211> LENGTH: 98
<212> TYPE: PRT
<213> ORGANISM: Homo sapiens

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 33
<211> LENGTH: 296
<212> TYPE: DNA
<213> ORGANISM: Homo sapiens

<400> SEQUENCE: 33
caggtgcagc tgcaggagtc gggcccagga ctggtgaagc cttcggggac cctgtccctc    60
acctgcgctg tctctggtgg ctccatcagc agtagtaact ggtggagttg ggtccgccag   120
cccccaggga aggggctgga gtggattggg gaaatctatc atagtgggag caccaactac   180
aacccgtccc tcaagagtcg agtcaccata tcagtagaca agtccaagaa ccagttctcc   240
ctgaagctga gctctgtgac cgccgcggac acggccgtgt attactgtgc gagaga        296

<210> SEQ ID NO 34
<211> LENGTH: 98
<212> TYPE: PRT
<213> ORGANISM: Homo sapiens

<400> SEQUENCE: 34

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80
```

```
Leu Lys Leu Ser Ser Val Thr Ala Ala Asp Thr Ala Val Tyr Tyr Cys
                85                  90                  95

Ala Arg

<210> SEQ ID NO 35
<211> LENGTH: 293
<212> TYPE: DNA
<213> ORGANISM: Homo sapiens

<400> SEQUENCE: 35
caggtgcagc tgcaggagtc gggcccagga ctggtgaagc cttcggagac cctgtccctc      60
acctgcactg tctctggtgg ctccatcagt agttactact ggagctggat ccggcagccc     120
ccagggaagg gactggagtg gattgggtat atctattaca gtgggagcac caactacaac     180
ccctccctca agagtcgagt caccatatca gtagacacgt ccaagaacca gttctccctg     240
aagctgagct ctgtgaccgc tgcggacacg gccgtgtatt actgtgcgag aga            293

<210> SEQ ID NO 36
<211> LENGTH: 97
<212> TYPE: PRT
<213> ORGANISM: Homo sapiens

<400> SEQUENCE: 36

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 37
<211> LENGTH: 290
<212> TYPE: PRT
<213> ORGANISM: Homo sapiens

<400> SEQUENCE: 37

Gly Ala Ala Ala Thr Thr Gly Thr Gly Thr Thr Gly Ala Cys Gly Cys
1               5                   10                  15

Ala Gly Thr Cys Thr Cys Cys Ala Gly Gly Cys Ala Cys Cys Cys Thr
            20                  25                  30

Gly Thr Cys Thr Thr Thr Gly Thr Cys Thr Cys Cys Ala Gly Gly Gly
        35                  40                  45

Gly Ala Ala Ala Gly Ala Gly Cys Cys Ala Cys Cys Cys Thr Cys Thr
    50                  55                  60

Cys Cys Thr Gly Cys Ala Gly Gly Gly Cys Cys Ala Gly Thr Cys Ala
65                  70                  75                  80

Gly Ala Gly Thr Gly Thr Thr Ala Gly Cys Ala Gly Cys Ala Gly Cys
                85                  90                  95

Thr Ala Cys Thr Thr Ala Gly Cys Cys Thr Gly Gly Thr Ala Cys Cys
```

```
                100              105              110
Ala Gly Cys Ala Gly Ala Ala Cys Cys Thr Gly Gly Cys Cys Ala
            115              120              125
Gly Gly Cys Thr Cys Cys Ala Gly Gly Cys Thr Cys Cys Thr Cys
            130              135              140
Ala Thr Cys Thr Ala Thr Gly Gly Thr Gly Cys Ala Thr Cys Ala
145              150              155              160
Gly Cys Ala Gly Gly Cys Cys Ala Cys Thr Gly Gly Cys Ala Thr
            165              170              175
Cys Cys Cys Ala Gly Ala Cys Ala Gly Gly Thr Thr Cys Ala Gly Thr
            180              185              190
Gly Gly Cys Ala Gly Thr Gly Gly Gly Thr Cys Thr Gly Gly Ala
            195              200              205
Cys Ala Gly Ala Cys Thr Thr Cys Ala Cys Thr Cys Thr Ala Cys
            210              215              220
Cys Ala Thr Cys Ala Gly Cys Ala Gly Ala Cys Thr Gly Gly Ala Gly
225              230              235              240
Cys Cys Thr Gly Ala Ala Gly Ala Thr Thr Thr Gly Cys Ala Gly
            245              250              255
Thr Gly Thr Ala Thr Thr Ala Cys Thr Gly Thr Cys Ala Gly Cys Ala
            260              265              270
Gly Thr Ala Thr Gly Gly Thr Ala Gly Cys Thr Cys Ala Cys Cys Thr
            275              280              285
Cys Cys
    290

<210> SEQ ID NO 38
<211> LENGTH: 96
<212> TYPE: PRT
<213> ORGANISM: Homo sapiens

<400> SEQUENCE: 38

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Pro
                85                  90                  95

<210> SEQ ID NO 39
<211> LENGTH: 288
<212> TYPE: DNA
<213> ORGANISM: Homo sapiens
<220> FEATURE:
<221> NAME/KEY: misc_feature
<222> LOCATION: (288)..(288)
<223> OTHER INFORMATION: n is a, c, g, or t

<400> SEQUENCE: 39
gacatccaga tgacccagtc tccatcctcc ctgtctgcat ctgtaggaga cagagtcacc        60
atcacttgcc gggcaagtca gggcattaga aatgatttag gctggtatca gcagaaacca      120
```

```
gggaaagccc ctaagcgcct gatctatgct gcatccagtt tgcaaagtgg ggtcccatca      180
aggttcagcg gcagtggatc tgggacagaa ttcactctca caatcagcag cctgcagcct      240
gaagattttg caacttatta ctgtctacag cataatagtt accctccn                   288
```

```
<210> SEQ ID NO 40
<211> LENGTH: 96
<212> TYPE: PRT
<213> ORGANISM: Homo sapiens

<400> SEQUENCE: 40
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Pro
                85                  90                  95

```
<210> SEQ ID NO 41
<211> LENGTH: 288
<212> TYPE: DNA
<213> ORGANISM: Homo sapiens

<400> SEQUENCE: 41
gacatccaga tgacccagtc tccatcctcc ctgtctgcat ctgtaggaga cagagtcacc       60
atcacttgcc gggcaagtca gagcattagc agctatttaa attggtatca gcagaaacca      120
gggaaagccc ctaagctcct gatctatgct gcatccagtt tgcaaagtgg ggtcccatca      180
aggttcagtg gcagtggatc tgggacagat ttcactctca ccatcagcag tctgcaacct      240
gaagattttg caacttacta ctgtcaacag agttacagta cccctcch                   288
```

```
<210> SEQ ID NO 42
<211> LENGTH: 96
<212> TYPE: PRT
<213> ORGANISM: Homo sapiens

<400> SEQUENCE: 42
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

```
<210> SEQ ID NO 43
```

<211> LENGTH: 293
<212> TYPE: DNA
<213> ORGANISM: Homo sapiens

<400> SEQUENCE: 43

```
caggtgcagc tgcaggagtc gggcccagga ctggtgaagc cttcggagac cctgtccctc    60
acctgcactg tctctggtgg ctccatcagt agttactact ggagctggat ccggcagccc   120
gccgggaagg gactggagtg gattgggcgt atctatacca gtgggagcac caactacaac   180
ccctccctca gagtcgagt caccatgtca gtagacacgt ccaagaacca gttctccctg    240
aagctgagct ctgtgaccgc cgcggacacg gccgtgtatt actgtgcgag aga           293
```

<210> SEQ ID NO 44
<211> LENGTH: 97
<212> TYPE: PRT
<213> ORGANISM: Homo sapiens

<400> SEQUENCE: 44

```
Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ser Tyr
            20                  25                  30
Tyr Trp Ser Trp Ile Arg Gln Pro Ala Gly Lys Gly Leu Glu Trp Ile
        35                  40                  45
Gly Arg Ile Tyr Thr Ser Gly Ser Thr Asn Tyr Asn Pro Ser Leu Lys
    50                  55                  60
Ser Arg Val Thr Met Ser Val Asp Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
Arg
```

<210> SEQ ID NO 45
<211> LENGTH: 470
<212> TYPE: PRT
<213> ORGANISM: Homo sapiens

<400> SEQUENCE: 45

```
Met Glu Phe Gly Leu Ser Trp Leu Phe Leu Val Ala Ile Leu Lys Gly
1               5                   10                  15
Val Gln Cys Glu Val Gln Leu Leu Glu Ser Gly Gly Gly Leu Val Gln
            20                  25                  30
Pro Gly Gly Ser Leu Arg Leu Ser Cys Thr Ala Ser Gly Phe Thr Phe
        35                  40                  45
Ser Ser Tyr Ala Met Asn Trp Val Arg Gln Ala Pro Gly Lys Gly Leu
    50                  55                  60
Glu Trp Val Ser Ala Ile Ser Gly Ser Gly Gly Thr Thr Phe Tyr Ala
65                  70                  75                  80
Asp Ser Val Lys Gly Arg Phe Thr Ile Ser Arg Asp Asn Ser Arg Thr
                85                  90                  95
Thr Leu Tyr Leu Gln Met Asn Ser Leu Arg Ala Glu Asp Thr Ala Val
            100                 105                 110
Tyr Tyr Cys Ala Lys Asp Leu Gly Trp Ser Asp Ser Tyr Tyr Tyr Tyr
        115                 120                 125
Tyr Gly Met Asp Val Trp Gly Gln Gly Thr Thr Val Thr Val Ser Ser
    130                 135                 140
```

```
Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
            165                 170                 175

Phe Pro Glu Pro Val Thr Val Ser Trp Asn Ser Gly Ala Leu Thr Ser
        180                 185                 190

Gly Val His Thr Phe Pro Ala Val Leu Gln Ser Ser Gly Leu Tyr Ser
    195                 200                 205

Leu Ser Ser Val Val Thr Val Pro Ser Ser Asn Phe Gly Thr Gln Thr
    210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Gln Phe Asn Trp Tyr Val Asp Gly
    290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val Val His Gln Asp Trp
                325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Thr Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Met Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 46
<211> LENGTH: 470
<212> TYPE: PRT
<213> ORGANISM: Homo sapiens

<400> SEQUENCE: 46

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45
```

-continued

Ser Ser Tyr Ala Met Ser Trp Val Arg Gln Ala Pro Gly Lys Gly Leu
         50                  55                  60

Glu Trp Val Ser Ala Ile Ser Gly Ser Gly Gly Ser Thr Tyr Tyr Ala
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
             100                 105                 110

Tyr Tyr Cys Ala Lys Gly Tyr Ser Ser Gly Trp Tyr Tyr Tyr Tyr Tyr
             115                 120                 125

Tyr Gly Met Asp Val Trp Gly Gln Gly Thr Thr Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Gln Phe Asn Trp Tyr Val Asp Gly
    290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val His Gln Asp Trp
                325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Thr Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Met Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

```
Ser Leu Ser Pro Gly Lys
465                 470
```

<210> SEQ ID NO 47
<211> LENGTH: 236
<212> TYPE: PRT
<213> ORGANISM: Homo sapiens

<400> SEQUENCE: 47

```
Met Asp Met Arg Val Pro Ala Gln Leu Leu Gly Leu Leu Leu Leu Trp
1               5                   10                  15

Phe Pro Gly Ala Arg Cys Asp Ile Gln Met Thr Gln Phe Pro Ser Ser
            20                  25                  30

Leu Ser Ala Ser Val Gly Asp Arg Val Thr Ile Thr Cys Arg Ala Ser
        35                  40                  45

Gln Gly Ile Arg Asn Asp Leu Gly Trp Tyr Gln Gln Lys Pro Gly Lys
    50                  55                  60

Ala Pro Lys Arg Leu Ile Tyr Ala Ala Ser Arg Leu His Arg Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys Leu Gln
            100                 105                 110

His Asn Ser Tyr Pro Cys Ser Phe Gly Gln Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 48
<211> LENGTH: 236
<212> TYPE: PRT
<213> ORGANISM: Homo sapiens

<400> SEQUENCE: 48

```
Met Asp Met Arg Val Pro Ala Gln Leu Leu Gly Leu Leu Leu Leu Trp
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Arg Asn Asp Leu Gly Trp Tyr Gln Gln Lys Pro Gly Lys
    50                  55                  60

Ala Pro Lys Arg Leu Ile Tyr Ala Ala Ser Ser Leu Gln Ser Gly Val
65                  70                  75                  80
```

-continued

```
Pro Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys Leu Gln
            100                 105                 110

His Asn Ser Tyr Pro Tyr Thr Phe Gly Gln Gly Thr Lys Leu Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 49
<211> LENGTH: 470
<212> TYPE: PRT
<213> ORGANISM: Homo sapiens

<400> SEQUENCE: 49

Met Glu Phe Gly Leu Ser Trp Val Phe Leu Val Ala Ile Ile Lys Gly
1               5                   10                  15

Val Gln Cys Gln Ala Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Asp Tyr Tyr Met Ser Trp Ile Arg Gln Ala Pro Gly Lys Gly Leu
    50                  55                  60

Glu Trp Val Ser Tyr Ile Ser Ser Ser Gly Ser Thr Arg Asp Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Val Arg Asp Gly Val Glu Thr Thr Phe Tyr Tyr Tyr Tyr
        115                 120                 125

Tyr Gly Met Asp Val Trp Gly Gln Gly Thr Thr Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220
```

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
            245                 250                 255

Pro Val Ala Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Gln Phe Asn Trp Tyr Val Asp Gly
290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val Val His Gln Asp Trp
                325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Thr Lys Gly Gln Pro Arg Glu
        355                 360                 365

Pro Gln Val Tyr Thr Leu Pro Pro Ser Arg Glu Glu Met Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Met Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 50
<211> LENGTH: 473
<212> TYPE: PRT
<213> ORGANISM: Homo sapiens

<400> SEQUENCE: 50

Met Glu Phe Gly Leu Ser Trp Val Phe Leu Val Ala Ile Ile Lys Gly
1               5                   10                  15

Val Gln Cys Gln Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Asp Tyr Tyr Met Ser Trp Ile Arg Gln Ala Pro Gly Lys Gly Leu
    50                  55                  60

Glu Trp Val Ser Tyr Ile Ser Ser Ser Gly Ser Thr Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Val Leu Arg Phe Leu Glu Trp Leu Leu Tyr Tyr

```
            115                 120                 125
Tyr Tyr Tyr Tyr Gly Met Asp Val Trp Gly Gln Gly Thr Thr Val Thr
            130                 135                 140

Val Ser Ser Ala Ser Thr Lys Gly Pro Ser Val Phe Pro Leu Ala Pro
145                 150                 155                 160

Cys Ser Arg Ser Thr Ser Glu Ser Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
                195                 200                 205

Leu Tyr Ser Leu Ser Ser Val Val Thr Val Pro Ser Ser Asn Phe Gly
            210                 215                 220

Thr Gln Thr Tyr Thr Cys Asn Val Asp His Lys Pro Ser Asn Thr Lys
225                 230                 235                 240

Val Asp Lys Thr Val Glu Arg Lys Cys Cys Val Glu Cys Pro Pro Cys
                245                 250                 255

Pro Ala Pro Pro Val Ala Gly Pro Ser Val Phe Leu Phe Pro Pro Lys
            260                 265                 270

Pro Lys Asp Thr Leu Met Ile Ser Arg Thr Pro Glu Val Thr Cys Val
            275                 280                 285

Val Val Asp Val Ser His Glu Asp Pro Glu Val Gln Phe Asn Trp Tyr
            290                 295                 300

Val Asp Gly Val Glu Val His Asn Ala Lys Thr Lys Pro Arg Glu Glu
305                 310                 315                 320

Gln Phe Asn Ser Thr Phe Arg Val Val Ser Val Leu Thr Val Val His
                325                 330                 335

Gln Asp Trp Leu Asn Gly Lys Glu Tyr Lys Cys Lys Val Ser Asn Lys
            340                 345                 350

Gly Leu Pro Ala Pro Ile Glu Lys Thr Ile Ser Lys Thr Lys Gly Gln
                355                 360                 365

Pro Arg Glu Pro Gln Val Tyr Thr Leu Pro Pro Ser Arg Glu Glu Met
            370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Met Leu Asp Ser Asp Gly Ser Phe Phe Leu
            420                 425                 430

Tyr Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
            450                 455                 460

Lys Ser Leu Ser Leu Ser Pro Gly Lys
465                 470

<210> SEQ ID NO 51
<211> LENGTH: 236
<212> TYPE: PRT
<213> ORGANISM: Homo sapiens

<400> SEQUENCE: 51

Met Asp Met Arg Val Pro Ala Gln Leu Leu Gly Leu Leu Leu Leu Trp
1               5                   10                  15
```

-continued

Phe Pro Gly Ala Arg Cys Asp Ile Gln Met Thr Gln Ser Pro Ser Ser
            20                  25                  30

Leu Ser Ala Ser Val Gly Asp Arg Val Thr Phe Thr Cys Arg Ala Ser
        35                  40                  45

Gln Asp Ile Arg Arg Asp Leu Gly Trp Tyr Gln Lys Pro Gly Lys
 50                  55                  60

Ala Pro Lys Arg Leu Ile Tyr Ala Ala Ser Arg Leu Gln Ser Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys Leu Gln
            100                 105                 110

His Asn Asn Tyr Pro Arg Thr Phe Gly Gln Gly Thr Glu Val Glu Ile
        115                 120                 125

Ile Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 52
<211> LENGTH: 236
<212> TYPE: PRT
<213> ORGANISM: Homo sapiens

<400> SEQUENCE: 52

Met Asp Met Arg Val Pro Ala Gln Leu Leu Gly Leu Leu Leu Leu Trp
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Arg Asn Asp Leu Gly Trp Tyr Gln Gln Lys Pro Gly Lys
 50                  55                  60

Ala Pro Lys Arg Leu Ile Tyr Ala Ala Ser Ser Leu Gln Ser Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys Leu Gln
            100                 105                 110

His Asn Ser Tyr Pro Trp Thr Phe Gly Gln Gly Thr Lys Val Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

```
Phe Tyr Pro Arg Glu Ala Lys Val Gln Trp Lys Val Asp Asn Ala Leu
            165                 170                 175

Gln Ser Gly Asn Ser Gln Glu Ser Val Thr Glu Gln Asp Ser Lys Asp
        180                 185                 190

Ser Thr Tyr Ser Leu Ser Ser Thr Leu Thr Leu Ser Lys Ala Asp Tyr
    195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 53
<211> LENGTH: 326
<212> TYPE: DNA
<213> ORGANISM: Artificial Sequence
<220> FEATURE:
<223> OTHER INFORMATION: Description of Artificial Sequence: Consensus
      Sequence
<220> FEATURE:
<221> NAME/KEY: misc_feature
<222> LOCATION: (289)..(289)
<223> OTHER INFORMATION: n is a, c, g, or t

<400> SEQUENCE: 53
gacatccaga tgacccagty tccatcctcc ctgtctgcat ctgtaggaga cagagtcacc      60
wtcacttgcc gggcaagtca ggrcattaga mrtgatttag ctggtwtca gcagaaacca     120 gggaaagcyc ctaagcgcct gatctatgct gcatccmrwt trcammgwgg ggtcccatca    180
aggttcagcg gcagtggatc tgggacagaa ttcactctca caatcagcmg cctgcagcct    240
gaagattttg caacttatta ctgtytacar cataatartt ayccyybsns kttyggcsrr    300
gggaccrags tggaratcaw acgaac                                          326

<210> SEQ ID NO 54
<211> LENGTH: 322
<212> TYPE: DNA
<213> ORGANISM: Artificial Sequence
<220> FEATURE:
<223> OTHER INFORMATION: Description of Artificial Sequence: Consensus
      Sequence

<400> SEQUENCE: 54
gacatccaga tgacccagtc tccatcctcc ctgtctgcat ctgyaggaga cagagtcacc      60
atcacttgcc gggcaagtca gagcattagy asctwtttaa attggtatca gcagaaacca    120
gggaaagccc ctaarctcct gatcyatgyt gcatccagtt trcaargtgg ggtcccatca    180
aggttcagtg gcagtggatc tgggacagat ttcactctca ccatcagcag tctgcaacct    240
gaagattttg caacttacta ctgtcaacag agttacartr ccccayychc tttcggcgga    300
gggaccaagg tggagatcaa ac                                              322

<210> SEQ ID NO 55
<211> LENGTH: 325
<212> TYPE: DNA
<213> ORGANISM: Artificial Sequence
<220> FEATURE:
<223> OTHER INFORMATION: Description of Artificial Sequence: Consensus
      Sequence
<220> FEATURE:
<221> NAME/KEY: misc_feature
<222> LOCATION: (291)..(291)
<223> OTHER INFORMATION: n is a, c, g, or t
```

-continued

```
<400> SEQUENCE: 55
gaaattgtgt tgacgcagtc tccaggcacc ctgtctttgt ctccagggga aagagccacc        60
ctctcctgya gggccagtca gagtgttmgc rgcagstact tagcctgta  ccagcagaaa       120 cctggccagg ctcccaggct cctcatctat ggtgcatcca gcagggccac tggcatccca       180
gacaggttca gtggcagtgg gtctgggaca gacttcactc tcaccatcag cagactggag       240
cctgaagatt ttgcagtgtw ttactgtcag cagtatggta gytcacctcs nacgttcggc       300
caagggacca aggtggaaat caaac                                             325

<210> SEQ ID NO 56
<211> LENGTH: 376
<212> TYPE: DNA
<213> ORGANISM: Artificial Sequence
<220> FEATURE:
<223> OTHER INFORMATION: Description of Artificial Sequence: Consensus
      Sequence

<400> SEQUENCE: 56
caggtgcagc tggtggagtc tgggggaggc ttggtcaagc ctggagggtc cctgagactc        60
tcctgtgcag cctctggatt cacyttcagt gactactaya tgagctggat ccgccaggct       120
ccagggaagg ggctggartg ggtttcatac attagtagta gtggtagtac cakakactac       180
gcagactctg tgaagggccc attcaccatc tccagggaca acgccaagaa ctcactgtat       240
ctgcaaatga acagcctgag agccgaggac acggccgtgt attactgtgy gagagatgga       300
gtggaaacta cttttactac ctactactac ggtatggacg tctggggcca agggaccacg       360
gtcaccgtct cctcag                                                       376

<210> SEQ ID NO 57
<211> LENGTH: 358
<212> TYPE: DNA
<213> ORGANISM: Artificial Sequence
<220> FEATURE:
<223> OTHER INFORMATION: Description of Artificial Seqence: Consensus
      Sequence
<220> FEATURE:
<221> NAME/KEY: misc_feature
<222> LOCATION: (337)..(337)
<223> OTHER INFORMATION: n is a, c, g, or t

<400> SEQUENCE: 57
caggtgcagc tgcaggagtc gggcccagga ctggtgaagc cttcggagac cctgtccctc        60
acctgcactg tctctggtgg ctccatcagt arttactact ggagctggat ccggcagccc       120
gccgggaagg gactggagtg gattgggcgt atctatacca gtgggagcmc caactacaac       180
ccctccctca agagtcgagt caccatgtca gtagacacgt ccaagaacca gttctccctg       240
aagctgarct ctgtgaccgc cgcggacacg gccgtgtatt actgtgcggt aacgattttt       300
ggagtggtta ttatctttga ctactggggc cagrganccc tggtcaccgt ctcctcag        358

<210> SEQ ID NO 58
<211> LENGTH: 418
<212> TYPE: DNA
<213> ORGANISM: Artificial Sequence
<220> FEATURE:
<223> OTHER INFORMATION: Description of Artificial Sequence: Consensus
      Sequence

<400> SEQUENCE: 58
caggtgcagc tgttggagtc tgggggaggc ttggtacagc ctgggggtc  cctgagactc        60
```

-continued

```
tcctgtrcag cctctggatt caacctttagc agctatgcca tgarctgggt ccgccaggct    120
ccagggaagg ggctggagtg ggtctcagst attastggka gtggtggtab yacatwctac    180
gcagactccg tgaagggccc gttcaccatc tccagagaca attccargam cacgctgtat    240
ctgcaaatga acagcctgag agccgaggac acggccgtat attactgtgc gaaagatctk    300
ggctrsksyg actyttacta ctactactac ggtatggacg tctggggcca agggacyacg    360
gtgattatga gttggttcga cccctggggc cagggaaccc tggtcaccgt ctcctcag     418
```

<210> SEQ ID NO 59
<211> LENGTH: 364
<212> TYPE: DNA
<213> ORGANISM: Artificial Sequence
<220> FEATURE:
<223> OTHER INFORMATION: Description of Artificial Sequence: Consensus
      Sequence <400> SEQUENCE: 59

```
caggtgcagc tgcaggagtc gggcccagga ctggtgaagc cttcggagac cctgtccctc     60
acctgcactg tctctggtgg ctccatcagt agttactact ggagytggat ccggcagccc    120
ccagggaagg gactggagtg gattgggtat atctattaca gtgggagcac caactacaac    180
ccctccctca agagtcgact caccatatca gtagacacgt ccaagaacca gttctccctg    240
aagctgagyt ctgtgaccgc tgcggacacg gccgtgtatt actgtgccag gacgtatagc    300
agttcgttct actactacgg tatggacgtc tggggccaag gaccacggt caccgtctcc    360 tcag                                                                   364
```

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Consensus
      Sequence <400> SEQUENCE: 60

```
Gly Gly Gly Gly Ser Gly Gly Gly Gly Ser Gly Gly Gly Gly Ser
1               5                   10                  15
```